(12) United States Patent
Claes et al.

(10) Patent No.: US 12,404,309 B2
(45) Date of Patent: Sep. 2, 2025

(54) HOST CELL FOR PRODUCING A PROTEIN OF INTEREST

(71) Applicant: LONZA LTD, Visp (CH)

(72) Inventors: Katrien Claes, Vevey (CH); James Graham, Oxford (GB); Sylwia Jozwiak, Slough (GB); Christoph Kiziak, Visp (CH)

(73) Assignee: LONZA LTD, Visp (CH)

( * ) Notice: Subject to any disclaimer, the term of this patent is extended or adjusted under 35 U.S.C. 154(b) by 421 days.

(21) Appl. No.: 16/968,719

(22) PCT Filed: Jan. 30, 2019

(86) PCT No.: PCT/EP2019/052218
§ 371 (c)(1),
(2) Date: Aug. 10, 2020

(87) PCT Pub. No.: WO2019/154686
PCT Pub. Date: Aug. 15, 2019

(65) Prior Publication Data
US 2020/0399325 A1    Dec. 24, 2020

(30) Foreign Application Priority Data
Feb. 12, 2018  (EP) .................................. 18156329

(51) Int. Cl.
*C07K 14/39*     (2006.01)
*C12N 15/81*     (2006.01)

(52) U.S. Cl.
CPC ............ *C07K 14/39* (2013.01); *C12N 15/815* (2013.01)

(58) Field of Classification Search
None
See application file for complete search history.

(56) References Cited

U.S. PATENT DOCUMENTS

| 6,153,424 A | 11/2000 | Raymond et al. |
| 9,534,039 B2 | 1/2017 | Brig ét al. |

FOREIGN PATENT DOCUMENTS

| CN | 102276704 A | 12/2011 |
| CN | 106604986 A | 4/2017 |
| EP | 2 258 855 A1 | 12/2010 |
| JP | 2012-510808 A | 5/2012 |
| JP | 2014-530016 A | 11/2014 |
| JP | 2017-511147 A | 4/2017 |
| WO | 1992/017595 A1 | 10/1992 |
| WO | 2008/128701 A2 | 10/2008 |
| WO | 2010/099195 A1 | 9/2010 |
| WO | 2011/053545 A1 | 5/2011 |
| WO | 2011/073883 A1 | 6/2011 |
| WO | 2013/050551 A1 | 4/2013 |
| WO | 2014/067926 A1 | 5/2014 |
| WO | 2014/139608 A1 | 9/2014 |
| WO | 2015/095568 A1 | 6/2015 |
| WO | 2017/021541 A1 | 2/2017 |

OTHER PUBLICATIONS

Valli, M., et al. 2016 FEMS Yeast Research 16(6): 1-12. (Year: 2016).*
Zahrl, R.J., et al. 2017 FEMS Yeast Research 17(7): 1-15. (Year: 2017).*
Naumov, G.I., et al. 2018 Antonie van Leeuwenhoek 111:1197-1207. (Year: 2018).*
Abad, Sandra et al., "Real-time PCR-based determination of gene copy numbers in Pichia pastoris," Biotechnol. J., 2010, vol. 5, No. 4, pp. 413-420.
Cereghino, Joan Lin et al., "Heterologous protein expression in the methylotrophic yeast *Pichia pastoris*," FEMS Microbiology Reviews, 2000, vol. 24, pp. 45-66.
Cos, Oriol et al., "Operational strategies, monitoring and control of heterologous protein production in the methylotrophic yeast *Pichia pastoris* under different promoters: A review," Microbial Cell Factories, 2006, vol. 5, No. 17, pp. 1-20.
Cregg, James M. et al., "Recombinant Protein Expression in Pichia pastoris," Molecular Biotechnology, 2000, vol. 16, No. 1, pp. 23-52.
Doneanu, Catalin E. et al., "Analysis of host-cell proteins in biotherapeutic proteins by comprehensive online two-dimensional liquid chromatography/mass spectrometry," mAbs, Jan./Feb. 2012, vol. 4, No. 1, pp. 24-44.
Gaj, Thomas et al., "ZFN, TALEN and CRISPR/Cas-based methods for genome engineering," Trends Biotechnol., Jul. 2013, vol. 31, No. 7, pp. 397-405.
Heiss, Silvia et al., "Identification and deletion of the major secreted protein of Pichia pastoris," Applied Microbial and Cell Physiology, 2013, vol. 97, pp. 1241-1249.
Huang, Chung-Jr et al., "A proteomic analysis of the Pichia pastoris secretome in methanol-induced cultures," Appl Microbiol Biotechnol, 2011, vol. 90, pp. 235-247.
Kurtzman, Cletus Paul et al., "Biotechnological strains of Komagataella (Pichia) pastoris are Komagataella phaffi as determined from multigene sequence analysis," J Ind Microbiol Biotechnol, 2009, vol. 36, pp. 1435-1438.
Mattanovich, Diethard et al., "Genome, secretome and glucose transport highlight unique features of the protein production host Pichia pastoris," Microbial Cell Factories, 2009, vol. 8, No. 29, pp. 1-13.
Silva, Jeffrey C. et al., "Absolute Quantification of Proteins by LCMSE," Mol Cell Proteomics, 2006, vol. 5, No. 1, pp. 144-156.
Stratton, Jayne et al., "High Cell-Density Fermentation," Methods in Molecular Biology, 1998, vol. 103, pp. 107-120.

(Continued)

*Primary Examiner* — Marsha Tsay
(74) *Attorney, Agent, or Firm* — MEDLER FERRO WOODHOUSE & MILLS PLLC

(57) ABSTRACT

A eukaryotic host cell engineered to produce a heterologous protein of interest (POI), which cell is genetically modified to reduce production of at least one of three different endogenous host cell protein (HCP), and its use in a method of producing the POI.

Figure 2:
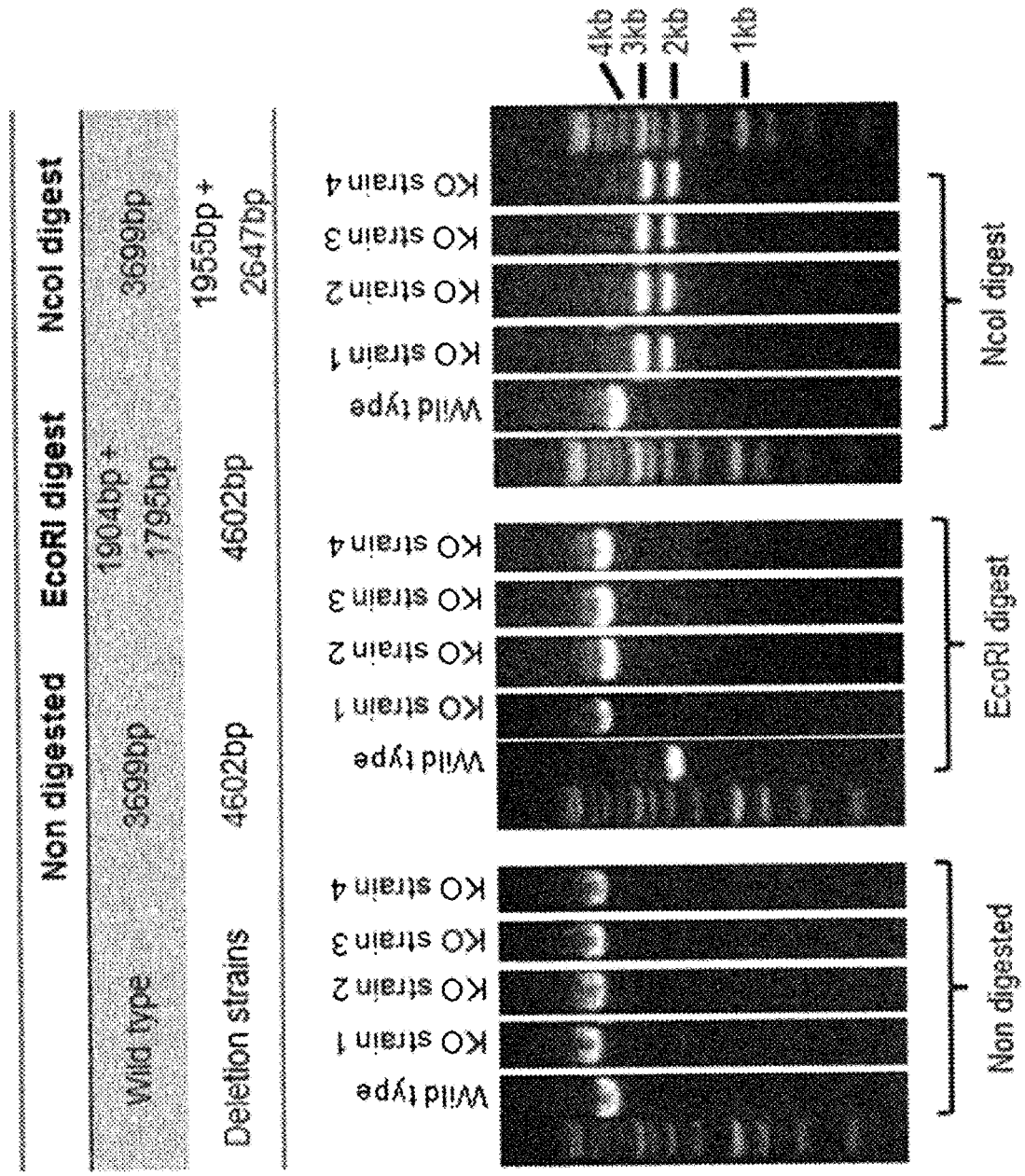

15 Claims, 8 Drawing Sheets
Specification includes a Sequence Listing.

(56) References Cited

OTHER PUBLICATIONS

Weninger, Astrid et al., "Combinatorial optimization of CRISPR/Cas9 expression enables precision genome engineering in the methylotrophic yeast Pichia pastoris," Journal of Biotechnology, 2016, vol. 235, pp. 139-149.
Zhang, Jing et al., "Peaks DB: De Novo Sequencing Assisted Database Search for Sensitive and Accurate Peptide Identification," Mol Cell Proteomics, 2012, vol. 11, No. 4, M111.010587, pp. 1-8.
Partial International Search Report mailed Feb. 20, 2019 in corresponding International Patent Application No. PCT/EP2019/052218.
International Search Report mailed Apr. 11, 2019 in corresponding International Patent Application No. PCT/EP2019/052218.
International Preliminary Report on Patentability mailed Aug. 18, 2020 in corresponding International Patent Application No. PCT/EP2019/052218.
International Written Opinion mailed Apr. 11, 2019 in corresponding International Patent Application No. PCT/EP2019/052218.
Foss et al., "Genetic basis of proteome variation in yeast," Nature Genetics 39(11):1369-1375 (2007).
Valgepea et al., "Lean-proteome strains-next step in metabolic engineering," Front. Bioeng. Biotechnol. 3(11):1-3 (2015).

\* cited by examiner

Fig. 1

SEQ ID NO:1

```
MKFAISTLLI ILQAAAVFAA FPISDITVVS ERTDASTAYL SDWFVVSFVF STAGSDETIA GDATIEVSIP
NELEFVQYPD SVDPSVSEFF TTAGVQVLST AFDYDSHVLT FTFSDPGQVI TDLEGVVFFT LKLSEQFTES
ASPGQHTFDF ETSDQTYSPS VDLVALDRSQ PIKLSNAVTG GVEWFVDIPG AFGDITNIDI STVQTPGTFD
CSEVKYAVGS SLNEFGDFTP QDRTTFFSNS SSGEWIPITP ASGLPVESFE CGDGTISLSF AGELADDEVL
RVSFLSNLAD DVLEVQNVVN VDLTTADSRK RALTSFVLDE PFYRASRTDT AAFEAFAAVP ADGDITSTST
AITSVTATVT HTTVTSVCYV CAETPVTVTY TAPVITNPIY YTTKVHVCNV CAETPITYTV TIPCETDEYA
PAKPTGTEGE KIVTVITKEG GDKYTKTYEE VTYTKTYPKG GHEDHIVTVK TKEGGEKVTK TYEEVTYTKG
PEIVTVVTKE GGEKVTTTYH DVPEVVTVIT KEGGEKVTTT YPATYPATYT EGHSAGVPTS ASTPPQATYT
VSEAQVNLGS KSAVGLLAIV PMLFLAI
```

SEQ ID NO:2

```
ATGAAGTTCGCAATTTCAACACTTCTTATTATCCTACAGGCTGCCGCTGTTTTTGCTGCCTTCCCTATATCTGATATCACAGTTG
TCAGTGAAAGAACTGACGCATCGACTGCCTATCTGTCGGACTGGTTTGTTGTTTCATTCGTTTTTAGCACTGCTGGCAGTGACGA
AACAATCGCTGGTGACGCTACTATTGAAGTCTCTATTCCTAATGAGCTAGAGTTTGTTCAATACCCTGATTCCGTTGACCCATCC
GTTTCCGAATTCTTTACAACCGCTGGTGTTCAAGTTTTGAGTACCGCATTTGATTATGACAGCCATGTTTTGACTTTCACTTTCT
CTGACCCAGGTCAAGTTATTACTGACCTTGAAGGAGTTGTTTTCTTTACACTCAAACTCAGTGAGCAGTTCACCGAGTCTGCTTC
CCCTGGCCAACACACCTTCGACTTCGAAACCTCTGATCAGACCTACAGTCCTTCTGTCGACTTGGTCGCACTTGACAGATCTCAG
CCAATCAAGCTGAGCAACGCTGTGACCGGTGGTGTTGAATGGTTTGTTGATATTCCAGGTGCATTTGGAGACATCACCAACATTG
ACATCAGCACTGTTCAGACCCCAGGTACCTTTGACTGTTCGGAGGTTAAGTATGCTGTCGGAAGCAGCCTGAACGAATTTGGTGA
CTTTACCCCACAGGATAGAACAACTTTCTTCAGCAATTCGTCCAGTGGAGAATGGATTCCAATTACTCCTGCTTCAGGTCTTCCA
GTTGAAAGCTTTGAGTGTGGTGATGGTACCATCTCTTTGAGCTTTGCCGGTGAATTAGCTGACGATGAAGTTCTTAGAGTTTCTT
TCCTATCAAACCTGGCTGATGATGTTCTTGAAGTTCAGAACGTTGTGAATGTTGACCTCACCACTGCAGACTCGCGTAAGAGAGC
ATTGACTTCGTTCGTCCTTGATGAGCCATTTTACCGTGCTAGCAGAACCGACACAGCTGCCTTCGAAGCTTTTGCAGCCGTACCA
GCTGACGGAGATATTACTTCTACTTCAACTGCCATTACCAGTGTTACTGCAACAGTTACCCACACCACTGTTACATCCGTCTGTT
ACGTTTGTGCTGAAACTCCTGTTACCGTTACCTACACCGCTCCAGTCATTACTAACCCAATTTACTATACCACTAAGGTTCACGT
TTGTAACGTCTGTGCTGAAACACCAATTACCTACACTGTTACCATTCCTTGTGAAACTGATGAATACGCTCCAGCTAAGCCAACT
GGCACTGAGGGTGAGAAGATCGTCACCGTTATTACAAAAGAAGGTGGTGACAAGTACACCAAGACATACGAAGAAGTCACTTACA
CCAAGACTTATCCCAAGGGTGGTCATGAGGACCATATTGTCACTGTCAAAACTAAAGAAGGTGGTGAAAAGGTCACTAAGACTTA
CGAGGAAGTCACCTATACCAAGGGTCCTGAAATTGTTACTGTTGTTACCAAGGAGGGTGGGGAGAAAGTTACCACTACTTACCAC
GATGTTCCTGAGGTTGTTACTGTTATCACCAAGGAAGGTGGAGAGAAAGTTACTACTACTTACCCAGCTACTTACCCAGCTACCT
ACACAGAAGGCCACAGTGCTGGAGTTCCAACAAGTGCTAGCACCCCTCCTCAAGCTACTTACACTGTGAGTGAGGCTCAAGTCAA
CTTGGGTTCCAAATCTGCTGTTGGTCTGTTAGCAATCGTCCCAATGCTCTTCTTGGCTATCTAA
```

Fig. 1 (continued)

SEQ ID NO:3

```
MQVKSIVNLL LACSLAVARP LEHAHHQHDK RGVVVVTKTI VVDGSTVEAT AAAQVQEHAE TFAESTPSAV
VSSSSAPSSA SSASAPASSG SFSAGTKGVT YSPYQAGGGC KTAEEVASDL SQLTGYEIIR LYGVDCNQVE
NVFKAKAPGQ KLFLGIFFVD AIESGVSAIA SAVKSYGSWD DVHTVSVGNE LVNNGEATVS QIGQYVSTAK
SALRSAGFTG PVLSVDTFIA VINNPGLCDF ADEYVAVNAH AFFDGGIAAS GAGDWAAEQI QRVSSACGGK
DVLIVESGWP SKGDTNGAAV PSKSNQQAAV QSLGQKIGSS CIAFNAFNDY WKADGPFNAE KYWGILDS
```

SEQ ID NO:4

```
ATGCAAGTTAAATCTATCGTTAACCTACTGTTGGCATGTTCGTTGGCCGTGGCCAGACCTTTGGAGCACGCCCACCATCAACATG
ACAAGAGAGGTGTTGTCGTCGTGACCAAGACCATCGTTGTCGATGGTTCCACCGTTGAGGCTACCGCAGCAGCCCAGGTCCAAGA
GCACGCTGAAACTTTCGCAGAGTCGACTCCTTCAGCTGTTGTTTCCAGTTCATCAGCTCCTTCCTCTGCTTCTTCTGCTTCCGCT
CCTGCCTCTTCCGGTAGCTTCTCCGCTGGAACCAAAGGTGTCACCTACTCTCCTTACCAAGCCGGTGGTGGCTGTAAGACTGCAG
AGGAGGTCGCTTCCGATCTTTCCCAGTTGACCGGCTACGAGATCATCAGATTGTACGGTGTTGACTGTAACCAAGTCGAGAACGT
CTTCAAGGCCAAGGCCCCAGGTCAAAAGTTGTTTTTGGGAATCTTCTTTGTTGATGCTATCGAGAGCGGTGTCAGTGCTATTGCC
TCCGCTGTCAAGTCATACGGTTCTTGGGACGATGTCCACACTGTCTCTGTTGGTAACGAGTTGGTCAACAACGGTGAGGCCACTG
TTTCCCAAATCGGTCAATACGTTTCTACCGCTAAATCTGCCTTGAGATCTGCTGGTTTCACCGGTCCAGTTCTTTCTGTCGACAC
TTTCATTGCTGTCATCAACAACCCCAGGGTTGTGTGACTTTGCTGACGAGTACGTTGCCGTTAACGCTCACGCTTTCTTTGACGGT
GGCATTGCTGCCTCTGGAGCTGGTGATTGGCTGCTGAGCAGATCCAAAGAGTTTCTTCCGCTTGTGGTGGCAAGGATGTCCTCA
TTGTCGAGTCCGGATGGCCTTCAAAGGGAGACACCAACGGTGCTGCCGTTCCTTCCAAGTCAAACCAACAGGCTGCTGTCCAATC
TCTAGGTCAGAAGATCGGTTCTTCTTGTATTGCTTTCAACGCTTTCAACGATTACTGGAAGGCCGATGGTCCTTTCAACGCTGAG
AAGTACTGGGGTATCCTAGACTCCTAA
```

SEQ ID NO 5:

```
MKISALTACA VTLAGLAIAA PAPKPEDCTT TVQKRHQHKR AVAYDYVYVT VTINGQGETI SPTVVAELET
VSTPATSSSA VATSSAPATT SSIPETTSAQ VTTSSVAEST SAQFTSSTEE ASSSVEQTTQ SSSSSSPSSS
SSSSSSSGSS SGSSSGGIDG DLSWYSGPGN KFQDGTIKCS EFPSGNGVVA LDHLGFGGWS GLYHPSDTST
GGICEPDTYC SYACQSGMSK TQWPSEQPDN GVSVGGLYCD SDGYLRSKK DTDYLCEWGI DVAYVVSEIG
KTAAICRTDY PGTENMVIPT VVSPGGELPL TTVDQSSYYT WRGMKTSAQY YVNDAGVDWT TGCTWGDYGT
DYGNWAPLNF GAGYDNGISY LSLIPNPNNK DSLNYNVKIV AYDDSSVVIG ECKYENGSYN GNGSDGCTVA
VNSGKAKFVL Y
```

Fig. 1 (continued)

SEQ ID NO 6:

ATGAAGATATCCGCTCTTACAGCCTGCGCTGTTACTCTAGCTGGTCTTGCAATTGCAGCACCAGCTCCAAAGCCTGAAGATTGTA
CTACTACAGTGCAGAAACGTCACCAACACAAACGTGCTGTCGCATACGATTACGTTTATGTCACAGTGACTATCAATGGCCAAGG
TGAAACCATTTCTCCAACTGTTGTGGCAGAACTTGAGACGGTTTCCACGCCTGCAACAAGCTCATCCGCAGTTGCAACTTCTTCT
GCTCCTGCAACCACTTCTTCAATCCCAGAGACAACTTCTGCACAAGTGACCACCTCTTCTGTTGCAGAGTCCACTTCAGCGCAAT
TCACTTCATCTACCGAAGAAGCCTCTTCTTCTGTTGAGCAAACGACTCAATCAAGTTCAAGTTCAAGTCCAAGTTCCAGTTCCAG
TTCAAGTTCGAGCTCAGGCTCTAGTTCAGGATCCAGTTCCGGTGGAATCGATGGAGACCTAAGCTGGTACTCAGGTCCTGGAAAC
AAATTCCAGGATGGTACTATAAAGTGTTCCGAGTTCCCATCCGGTAACGGTGTTGTTGCCTTGGACCATCTCGGATTCGGAGGAT
GGTCAGGATTATACCACCCATCTGATACCTCTACTGGTGGGATCTGTGAACCAGACACCTACTGCTCTTATGCCTGCCAATCAGG
TATGTCGAAGACACAATGGCCATCTGAACAACCGGACAATGGTGTTTCCGTTGGTGGTCTGTATTGTGATTCTGATGGATACCTT
TACCGTTCCAAGAAAGACACTGACTATCTATGTGAATGGGGTATTGATGTCGCCTATGTTGTCAGTGAAATTGGTAAAACTGCTG
CCATCTGTAGAACCGACTATCCAGGAACTGAAAACATGGTTATACCAACTGTTGTGAGTCCGGGTGGAGAACTCCCTCTGACAAC
AGTTGACCAATCCTCTTACTATACGTGGAGGGGAATGAAGACTTCGGCCCAATACTACGTGAACGATGCTGGTGTTGACTGGACC
ACCGGTTGTACCTGGGGAGACTATGGAACCGACTACGGTAACTGGGCGCCATTGAACTTTGGTGCCGGTTACGACAACGGCATTT
CATACCTTTCTTTAATCCCTAACCCTAACAACAAGGACTCCTTGAACTATAATGTCAAGATTGTTGCTTATGATGATTCTTCTGT
CGTTATCGGCGAGTGCAAGTATGAAAATGGTTCATACAATGGAAACGGTTCCGACGGTTGTACCGTTGCTGTCAACAGCGGTAAG
GCCAAGTTTGTGTTGTATTAA

SEQ ID NO 7:

MKLSTNLILA IAAASAVVSA APVAPAEEAA NHLHKRAYYT DTTKTHTFTE VVTVYRTLKPG ESIPTDSPSH
GGKSTKKGKG STTHSGAPGA TSGAPTDDTT STSGSVGLPT SATSVTSSTS SASTTSSGTSA TSTGTGTSTS
TSTGTGTGTT GTGTTSSSTS SSATSTPTGS IDAISQTLLD THNDKRALHG VPDLTWSTELA DYAQGYADSY
TCGSSLEHTG GPYGENLASG YSPAGSVEAW YNEISDYDFS NPGYSAGTGH FTQVVWKSTTQ LGCGYKECST
DRYYIICEYA PRGNIVSAGY FEDNVLPPV

SEQ ID NO 8:

ATGAAGCTCTCCACCAATTTGATTCTAGCTATTGCAGCAGCTTCCGCCGTTGTCTCAGCTGCTCCAGTTGCTCCAGCCGAAGAGG
CAGCAAACCACTTGCACAAGCGTGCTTACTACACCGACACAACCAAGACTCACACTTTCACTGAGGTTGTTACTGTCTACCGAAC
TTTGAAACCGGGCGAAAGTATCCCAACTGACTCTCCAAGCCACGGTGGTAAAAGTACTAAAAAGGGTAAGGGTAGTACCACTCAC
TCTGGTGCTCCAGGAGCTACCTCTGGTGCTCCAACTGACGACACCACTTCGACTAGTGGCTCAGTAGGGTTACCAACTAGCGCAA
CTTCAGTTACCTCTTCTACCTCCTCTGCAAGTACAACAAGCAGTGGAACTTCAGCCACTAGCACTGGTACCGGTACTAGCACTAG
CACTAGCACTGGTACTGGTACTGGTACTACAGGCACAGGAACCACTAGTTCCAGCACTAGCTCTTCTGCTACTTCGACTCCAACC
GGTTCTATCGACGCTATCAGCCAGACACTTCTGGATACTCACAATGATAAGCGTGCTTTGCACGGCGTCCCAGACCTTACTTGGT
CTACCGAACTCGCTGACTACGCCCAAGGTTACGCCGATTCATACACTTGTGGCTCTTCATTAGAACACACAGGTGGACCATACGG
TGAAAATTTGGCCTCTGGATACTCTCCTGCTGGCAGTGTAGAAGCATGGTACAACGAGATCAGCGACTACGATTTCTCTAACCCA
GGTTATTCTGCTGGTACCGGTCACTTCACCCAAGTTGTCTGGAAATCAACTACACAGCTGGGCTGTGGATACAAGGAGTGCAGTA
CCGACAGATACTACATCATCTGCGAATACGCACCTCGTGGAAATATTGTTTCTGCCGGCTACTTCGAAGACAACGTCCTGCCTCC
TGTT

Fig. 1 (continued)

SEQ ID NO:20

```
  1 mqlrvsfsfd yknggypwty fdfphtvthl imkfaiptlf vilqaasvfa afpitditvv
 61 sertdasiay lsdwflvsfv fstagsdetl agdatievsi pdelefvqyp esvdpsvsef
121 fttagvqvls tafdydshvl tftfsdpgqv itelegvvyf tlklseqfte satpgqhtfd
181 fetsdqvysp svdlvaldrt qpiklsnavt ggvewfvdip gafgditnid istvqtpgtf
241 dcsevkyavg sslnefgdft pqdrttffsn sssgewipit pasglpvesf ecgdgtisls
301 fageladdev lrvsflsnld ddvlevqnvv nvdlttadsr kraltsfvld epfyrasrtd
361 paafeafaav padgdittts tattsvtatv tettvtsvcy vcaetpvtvt ytapvitnpi
421 yyttkvhvcn vcaetpityt vtipcesdey apakptgtkg ekivtvvtke ggdkytktye
481 evtytktypk egghedhivt vttkeggekv tktyeevtyt kgpeivtvvt keggeevtkt
541 yhdvpevvtv vtkeggekvt ttypatyteg pgavptssva ppkatytvse advnlgsrsa
601 avgllailpm lflav
```

SEQ ID NO:21

```
  1 mqvksivnll lacslavarp lehahhqhdk rgvvvvtkti ivdgstveat aaaqvqehae
 61 tiaestpsav vassaapsaa ssasapassg sfsagtkgvt yspyqagggc ktaeevasdl
121 sqltdyeiir lygvdcnqve nvfkakapgq klflgiffvd aiesgvsaia savssygswn
181 dvhtvsvgne lvnngeatvs qigqyvstak salrsagftg pvlsvdtfia vinnpglcdf
241 adeyvavnah affdghiaas gagdwaaeqi qrvssacggk dvlivesgwp skgdtngaav
301 psksnqqaav qslgqkigss ciafnafndy wkadgpfnae kywgilds
```

SEQ ID NO:22

```
  1 mkisaltaca vtlaglaiaa papkpedctt tvqkrhqhkr avaydyvyvt vtingqgeti
 61 sptvvaelet astpatsssa hvetssapat tssvpettsa eqttssaett saqvtssvqe
121 tsssaeeqvt qssssssspss ssssssgsss gsssggidgd lswysgpgnk fqdgtikcse
181 fpsgngvval dhlgfggwsg lyhpsdtstg gicepdtycs yacqsgmskt qwpseqpdng
241 vsvgglycds dgylyrsktd tdylcewgid vayvvseigk taaicrtdyp gtenmviptv
301 vtpggelplt tvdqssyytw rgmktsaqyy vndagvdwtt gctwgdygtd ygnwaplnfg
361 agydngisyl slipnpnnkd tmnynvkiva yddssvvige ckyengsyng ngsdgctvav
421 nsgkakfvly
```

SEQ ID NO:23

```
  1 mkfstnlila iaaastvvsa apvapaeeaa nhlhkrayyt dttkthtfte vvtvyrtlkp
 61 gesiptgsps hggkgsktgk gkgsttdagv pgttsvapta dstsasgsig lptsassats
121 atssasttts gtstsstgtg tttgattgtg tsstgttsss tsssatstpt gsldaisqsl
181 ldthnekral hgvsdltwst eladyaqgya dsftcgsslv htggpygenl asgyspagsv
241 eawyneisdy dfsnpgysag tghftqvvwk sttqlgcgyk ecgtnryyii ceyaprgniv
301 sagyfednvl plv
```

Fig. 1 (continued)

SEQ ID NO:24

```
>SCW10 YMR305C SGDID:S000004921
MRFSNFLTVSALLTGALGAPAVRHKHEKRDVVTATVHAQVTVVVSGNSGETIVPVNENAV
VATTSSTAVASQATTSTLEPTTSANVVTSQQQTSTLQSSEAASTVGSSTSSSPSSSSSTS
SSASSSASSSISASGAKGITYSPYNDDGSCKSTAQVASDLEQLTGFDNIRLYGVDCSQVE
NVLQAKTSSQKLFLGIYYVDKIQDAVDTIKSAVESYGSWDDITTVSVGNELVNGGSATTT
QVGEYVSTAKSALTSAGYTGSVVSVDTFIAVINNPDLCNYSDYMAVNAHAYFDENTAAQD
AGPWVLEQIERVYTACGGKKDVVITETGWPSKGDTYGEAVPSKANQEAAISSIKSSCGSS
AYLFTAFNDLWKDDGQYGVEKYWGILSSD*
```

SEQ ID NO:25

```
>SCW4 YGR279C SGDID:S000003511
MRLSNLIASASLLSAATLAAPANHEHKDKRAVVTTTVQKQTTIIVNGAASTPVAALEENA
VVNSAPAAATSTTSSAASVATAAASSSENNSQVSAAASPASSSAATSTQSSSSSQASSSS
SSGEDVSSFASGVRGITYTPYESSGACKSASEVASDLAQLTDFPVIRLYGTDCNQVENVF
KAKASNQKVFLGIYYVDQIQDGVNTIKSAVESYGSWDDVTTVSIGNELVNGNQATPSQVG
QYIDSGRSALKAAGYTGPVVSVDTFIAVINNPELCDYSDYMAVNAHAYFDKNTVAQDSGK
WLLEQIQRVWTACDGKKNVVITESGWPSKGETYGVAVPSKENQKDAVSAITSSCGADTFL
FTAFNDYWKADGAYGVEKYWGILSNE*
```

SEQ ID NO:26

```
>SUN4 YNL066W SGDID:S000005010
MKLSATTLTAASLIGYSTIVSALPYAADIDTGCTTTAHGSHQHKRAVAVTYVYETVTVDK
NGQTVTPTSTEASSTVASTTTLISESSVTKSSSKVASSSESTEQIATTSSSAQTTLTSSE
TSTSESSVPISTSGSASTSSAASSATGSIYGDLADFSGPYEKFEDGTIPCGQFPSGQGVI
PISWLDEGGWSGVENTDTSTGGSCKEGSYCSYACQPGMSKTQWPSDQPSDGRSIGGLLCK
DGYLYRSNTDTDYLCEWGVDAAYVVSELSNDVAICRTDYPGTENMVIPTYVQAGDSLPLT
VVDQDTYYTWQGLKTSAQYYVNNAGISVEDACWGSSSSGVGNWAPLNFGAGSSDGVAYL
SLIPNPNNGNALNFNVKIVAADDSSTVNGECIYENGSFSGGSDGCTVSVTAGKAKFVLYN
*
```

HOST CELL FOR PRODUCING A PROTEIN OF INTEREST

TECHNICAL FIELD

The invention refers to protein production in a eukaryotic host cell, which host cell is engineered to reduce impurities in the host cell culture.

BACKGROUND

Proteins produced in eukaryotic cell culture have become increasingly important as diagnostic and therapeutic agents. For this purpose, cells are engineered and/or selected to produce unusually high levels of a recombinant or heterologous protein of interest. Optimization of cell culture conditions is important for successful commercial production of recombinant or heterologous proteins. Byproducts released from the host cell as host cell protein (HCP) and accumulated in the culture represent difficulties for purification of recombinant or heterologous proteins or can pose risks to product efficacy or patient safety.

Besides mammalian host cells, yeasts and filamentous fungi are commonly used as production hosts for biopharmaceutical proteins as well as for bulk chemicals. Methylotrophic yeast, such as *Pichia pastoris*, is well reputed for efficient secretion of heterologous proteins. *P. pastoris* has been reclassified into a new genus, *Komagataella*, and split into three species, *K. pastoris*, *K. phaffii*, and *K. pseudopastoris*. Strains commonly used for biotechnological applications belong to two proposed species, *K. pastoris* and *K. phaffii*. The strains GS115, X-33, CBS2612, and CBS7435 are *K. phaffii*, while the SMD series of protease deficient strains (e.g., SMD1168) is classified into the type species, *K. pastoris*, which is the reference strain for all the available *P. pastoris* strains. (Mattanovich et al. 2009, Microb Cell Fact. 8: 29; Kurtzman 2009, J Ind Microbiol Biotechnol. 36(11): 1435-8).

Biotechnological strains of *Komagataella* (*Pichia*) *pastoris* are *Komagataella phaffii* as determined from multigene sequence analysis.

Mattanovich et al. (Microbial Cell Factories 2009, 8:29 doi:10.1186/1475-2859-8-29) describe the genome sequencing of the type strain DSMZ 70382 of *K. pastoris*, and analyzed its secretome and sugar transporters.

Huang et al. (Appl Microbiol Biotechnol. 2011 April; 90(1):235-47. doi: 10.1007/s00253-011-3118-5. Epub 2011 Feb. 9) describe proteomic analysis of the *Pichia pastoris* secretome in methanol-induced cultures, identifying proteins secreted or released into the culture media in the methanol-induced fermentation cultures of *P. pastoris* X-33.

Heiss et al. (Appl Microbiol Biotechnol. 2013 February; 97(3):1241-9. doi: 10.1007/s00253-012-4260-4. Epub 2012 Jul. 17) have identified an extracellular protein X 1 (Epx1) as a major contaminating host cell protein of *Pichia pastoris* producing an antibody Fab fragment. EPX1 was found not to be generally upregulated but only in different stress situations. A respective deletion strain (Δepx1) was produced and found more susceptible than the wild type to the cell wall damaging agents Calcofluor white and Congo red, indicating that Epx1 may have a protective role for the cell wall. No significant difference in growth and product formation was observed between the wild type and the Δepx1 strain.

However, we have found out that Epx1p is not a highly abundant protein, amounting to less than around 3% (mol/mol) of total HCP in a *P. pastoris* cell culture.

HCPs are proteins that are produced or encoded by cells or organisms that are used in the production process and are unrelated to the intended product. Some are necessary for growth, survival, and normal cellular processing whereas others may be non-essential. Regardless of the utility, or lack thereof, HCPs are generally undesirable in a final drug substance. Though commonly present in small quantities (ppm, expressed as nanograms per milligrams of the intended protein) much effort and cost is expended by industry to remove them.

There is a need for the development of improved host cells suitable for production and/or purification of heterologous and/or recombinant proteins.

SUMMARY OF THE INVENTION

It is the object of the invention to provide host cells which are modified to give rise to a reduced level of HCP impurities when producing a recombinant or heterologous protein. Another object of the invention is to provide a method for producing a recombinant or heterologous protein in a host cell, wherein the risk of contamination of the recombinant or heterologous protein with HCP impurities is reduced.

The object is solved by the subject matter as claimed.

According to the invention, there is provided a eukaryotic host cell engineered to produce a heterologous protein of interest (POI), which cell is genetically modified to reduce production of at least one endogenous host cell protein (HCP) selected from the group consisting of a first HCP (HCP1), a second HCP (HCP2), and a third HCP (HCP3), wherein a) HCP1 comprises the amino acid sequence identified as SEQ ID NO:1, if the host cell is *Komagataella phaffii*, or its homologous sequence that is endogenous to the host cell if of another species;

b) HCP2 comprises the amino acid sequence identified as SEQ ID NO:3, if the host cell is *Komagataella phaffii*, or its homologous sequence that is endogenous to the host cell if of another species; and c) HCP3 comprises the amino acid sequence identified as SEQ ID NO:5, if the host cell is *Komagataella phaffii*, or its homologous sequence that is endogenous to the host cell if of another species.

According to a specific aspect, the cell is further genetically modified to reduce production of a further HCP which is HCP4, wherein d) HCP4 comprises the amino acid sequence identified as SEQ ID NO:7, if the host cell is *Komagataella phaffii*, or its homologous sequence that is endogenous to the host cell if of another species.

Specifically, said at least one HCP includes any one, two or three of HCP1, HCP2, HCP3. In addition, said at least one HCP specifically includes HCP4.

Specifically, said at least one HCP is HCP1, and optionally or additionally HCP2 and/or HCP3 and/or HCP4. Specific embodiments refer to the reduction of two or more HCPs, including HCP1. Specifically, said at least one HCP includes HCP1 and any one, two or three of HCP2, HCP3, or HCP4.

Yet specifically, said at least one HCP is HCP2, and optionally HCP1 and/or HCP3 and/or HCP4.

Yet specifically, said at least one HCP is HCP3, and optionally HCP1 and/or HCP2 and/or HCP4.

Specific embodiments refer to the reduction of two or more HCPs, e.g. HCP1 and HCP2, or HCP1 and HCP3, or HCP2 and HCP3.

Specific embodiments refer to the reduction of two or more HCPs, including reduction of any of: HCP1 and HCP4, or HCP2 and HCP4, or HCP3 and HCP4.

Specifically, SEQ ID NOs:1, 3, 5, and 7, are each wild-type (native) endogenous sequences of *K. phaffii*.

Specifically, the respective homologous sequence is of a species other than *K. phaffii*, e.g., of a yeast or filamentous fungal cell, preferably yeast of the *Komagataella* or *Pichia* genus, or *Saccharomyces* genus or any methylotrophic yeast.

According to a specific aspect, the host cell is
a) a yeast cell of a genus selected from the group consisting of *Pichia, Hansenula, Komagataella, Saccharomyces, Kluyveromyces, Candida, Ogataea, Yarrowia*, and *Geotrichum*, such as *Pichia pastoris, Komagataella phaffii, Komagataella pastoris, Komagataella pseudopastoris, Saccharomyces cerevisiae, Ogataea minuta, Kluyveromces lactis, Kluyveromes marxianus, Yarrowia lipolytica* or *Hansenula polymorpha*; or
b) a cell of filamentous fungi, such as *Aspergillus awamori* or *Trichoderma reesei*.

Yet, for the purpose described herein, the respective HCPs may be reduced in a host cell which is any one of an animal cell, a vertebrate cell, a mammalian cell, a human cell, a plant cell, a nematodal cell, an invertebrate cell such as an insect cell or a mollusk cell, or a stem cell derived of any of the foregoing, in particular any fungal cell or a yeast cell.

The respective homologous sequence is understood to be endogenous to the host cell which is used as host cell producing the POI as further described herein.

For example, if the host cell is *K. phaffii*, HCP1 is characterized by SEQ ID NO:1. Yet, if the host cell is of a different species (other than *K. phaffii*), the HCP1 sequence which is endogenous to the host cell is homologous to SEQ ID NO:1, e.g. the orthologous sequence of SEQ ID NO:1.

Likewise, if the host cell is *K. phaffii*, HCP2 is characterized by SEQ ID NO:3. Yet, if the host cell is of a different species (other than *K. phaffii*), the HCP2 sequence which is endogenous to the host cell is homologous to SEQ ID NO:3, e.g. the orthologous sequence of SEQ ID NO:3.

Likewise, if the host cell is *K. phaffii*, HCP3 is characterized by SEQ ID NO:5. Yet, if the host cell is of a different species (other than *K. phaffii*), the HCP3 sequence which is endogenous to the host cell is homologous to SEQ ID NO:5, e.g. the orthologous sequence of SEQ ID NO:5.

Likewise, if the host cell is *K. phaffii*, HCP4 is characterized by SEQ ID NO:7. Yet, if the host cell is of a different species (other than *K. phaffii*), the HCP4 sequence which is endogenous to the host cell is homologous to SEQ ID NO:7, e.g. the orthologous sequence of SEQ ID NO:7.

Specifically, any or each of the homologous sequences is characterized by at least 50% sequence identity to the respective amino acid sequence in *K. phaffii*, specifically at least any one of at least 50%, 60%, 70%, 80%, 90%, or 95% sequence identity.

Specifically, any or each of the homologous sequences is characterized by the same qualitative function e.g. as structural protein or as enzyme, though its quantitative activity might be different, compared to the respective amino acid sequence in *K. phaffii*.

Specifically, the host cell is genetically modified by one or more genetic modifications comprising genomic mutation(s) that reduce the expression of the polynucleotide(s) encoding said at least one HCP.

Specifically, the one or more genetic modifications comprise genomic mutation(s) which reduce the expression of a first and/or a second and/or a third endogenous polynucleotide, wherein
the first endogenous polynucleotide encodes the HCP1;
the second endogenous polynucleotide encodes HCP2; and
the third endogenous polynucleotide encodes HCP3.

Optionally and in addition, the host cell is further modified to introduce genomic mutation(s) which reduce the expression of a further endogenous polynucleotide, wherein
said further endogenous polynucleotide encodes the HCP4.

Specifically, each of the endogenous polynucleotides encoding the respective HCP is a wild-type (native) endogenous polynucleotide with a sequence that is naturally-occurring in the host cell.

Specifically, the endogenous polynucleotide encoding HCP1 in *K. phaffii* comprises SEQ ID NO:2. Yet, if the host cell is of a different species (other than *K. phaffii*), the HCP1 encoding sequence which is endogenous to the host cell is homologous to SEQ ID NO:2, e.g. the orthologous sequence of SEQ ID NO:2.

Specifically, the endogenous polynucleotide encoding HCP2 in *K. phaffii* comprises SEQ ID NO:4. Yet, if the host cell is of a different species (other than *K. phaffii*), the HCP2 encoding sequence which is endogenous to the host cell is homologous to SEQ ID NO:4, e.g. the orthologous sequence of SEQ ID NO:4.

Specifically, the endogenous polynucleotide encoding HCP3 in *K. phaffii* comprises SEQ ID NO:6. Yet, if the host cell is of a different species (other than *K. phaffii*), the HCP3 encoding sequence which is endogenous to the host cell is homologous to SEQ ID NO:6, e.g. the orthologous sequence of SEQ ID NO:6.

Specifically, the endogenous polynucleotide encoding HCP4 in *K. phaffii* comprises SEQ ID NO:8. Yet, if the host cell is of a different species (other than *K. phaffii*), the HCP4 encoding sequence which is endogenous to the host cell is homologous to SEQ ID NO:8, e.g. the orthologous sequence of SEQ ID NO:8.

Specifically, the host cell is genetically modified by one or more genetic modifications of the host cell genome comprising a disruption, substitution, deletion or knockout of (i) one or more endogenous polynucleotides, or a part thereof; or (ii) an expression control sequence of said one or more endogenous polynucleotides, preferably wherein said expression control sequence is selected from the group consisting of a promoter, a ribosomal binding site, transcriptional or translational start and stop sequences, an enhancer and activator sequence.

Specifically, the genetic or knockout modification includes one or more genomic mutations including deletion or inactivation of a gene or genomic sequence which reduces expression of a gene or part of a gene by at least 50%, 60%, 70%, 80%, 90%, or 95%, or even abolishes its expression, as compared to the respective host without such genetic modification.

Specifically, the genetic modification includes at least one modification of expression control sequences, such as a deletion or inactivation of a promoter, enhancer, signal, leader, or any other regulatory sequences, in particular those which control the expression and/or secretion of a protein. Specifically, the expression control sequences are operably linked to the relevant protein encoding gene.

Specifically, the one or more genetic modifications comprise genomic mutations which constitutively impair or otherwise reduce the expression of one or more endogenous polynucleotides.

Specifically, the one or more genetic modifications comprise genomic mutations introducing one or more inducible or repressible regulatory sequences which conditionally impair or otherwise reduce the expression of one or more endogenous polynucleotides. Such conditionally active modifications are particularly targeting those regulatory elements and genes which are active and/or expressed dependent on cell culture conditions.

Specifically, a gene encoding any of said at least one HCP is knocked out by said one or more genetic modifications.

Specifically, the expression of said one or more endogenous polynucleotides is reduced when producing the POI. Specifically, upon genetic modification, expression of said one or more endogenous polynucleotides encoding the at least one HCP is reduced under conditions of the host cell culture during which the POI is produced.

Specifically, the host cell is genetically modified to reduce the amount of any or each of said at least one HCP by at least any one of 50%, 60%, 70%, 80%, 90%, or 95%, (mol/mol) compared to the host cell without said modification, or even by 100%, thereby abolishing production of the respective HCP. Specifically, the amount of each of HCP1 and any one, two, or three of HCP2, HCP3, or HCP4, is reduced by at least any one of 50%, 60%, 70%, 80%, 90%, 95%, or 100% (mol/mol) compared to the host cell without said modification. According to a specific embodiment, such reduction is achieved by a knockout of a gene encoding any of said at least one HCP.

Therefore, according to a specific embodiment, once the host cell described herein is cultured in a cell culture, the amount of total HCP in the cell culture supernatant is reduced by at least any of 5%, or 10%, or even by at least 15% (mol/mol), compared to the amount of total HCP in the culture supernatant when culturing the comparable host cell without said genetic modification.

Total host cell protein (HCP) in a cell culture refers to the sum of all individual proteins derived from the cells expressing the POI but excluding the POI, and present in the cell culture supernatant once cells are separated from the cell culture media be e.g. centrifugation.

Specifically, the host cell is genetically modified to reduce the amount of said at least one HCP to less than any one of 10%, or 5%, or 3% (mol/mol) of total HCP in the cell culture supernatant.

Specifically, the amount of each of said at least one HCP described herein is reduced to less than 1% (mol/mol) of total HCP in the cell culture supernatant, or abolished, e.g., as determined by mass spectrometry analysis.

Specifically, the amount of total HCP in the cell culture supernatant is reduced by at least 5%, or at least 10% (mol/mol) as compared to the cell culture of the comparable host cell without said genetic modification.

By reducing the production of said at least one HCP the amount (e.g., the level or concentration, in particular the amount relative to a reference or total HCP) of said at least one HCP obtained in the cell culture supernatant is reduced.

When comparing the host cell described herein for the effect of said genetic modification to reduce production of said at least one HCP, it is typically compared to the comparable host cell without such genetic modification. Comparison is typically made with the same host cell type without such genetic modification, which is engineered to produce the recombinant or heterologous POI, in particular when cultured under conditions to produce said POI. Alternatively, comparison is made with the same host cell type which is not further engineered to produce the recombinant or heterologous POI.

According to a specific aspect, the reduction of said at least one HCP is determined by the reduction of the amount (e.g., the level or concentration, or the relative amount to a reference or to total HCP) of said at least one HCP in the cell culture supernatant. Specifically, the amount of each individual HCP or the amount of total HCP is determined by a suitable method, such as employing an ELISA assay, HPLC, capillary electrophoresis such as SDS-PAGE, or mass spectrometry, in particular wherein mass spectrometry is liquid chromatography-mass spectrometry (LC-MS), or liquid chromatography tandem-mass spectrometry (LC-MS/MS) e.g., as described by Doneanu et al. (MAbs. 2012; 4(1): 24-44).

Specifically, the host cell is provided which is capable of producing a reduced amount of HCPs as a byproduct besides the POI. HCPs include endogenous proteins present independent of a specific POI production process or process-specific proteins, which are impurities or contaminants in a POI preparation, such as a preparation of the cell culture supernatant comprising the POI, or a preparation obtained upon purifying the POI from a cell culture supernatant.

According to a specific embodiment, the host cell is genetically modified to comprise one or more deletions of (one or more) genomic sequences. Such host cell is typically provided as a deletion strain.

According to a specific aspect, the host cell described herein comprises an expression cassette comprising one or more regulatory nucleic acid sequences operably linked to a nucleotide sequence encoding the POI, in particular wherein said one or more operably linked sequences are not naturally associated with the POI encoding sequence.

Specifically, the expression cassette comprises a promoter operably linked to the POI encoding gene, and optionally signal and leader sequences, as necessary to express and produce the POI as a secreted protein.

Specifically, the expression cassette comprises a constitutive or inducible or repressible promoter.

Specific examples of constitutive promoter include e.g., the pGAP and functional variants thereof, any of the constitutive promoter such as pCS1, published in WO2014139608.

Specific examples of inducible or repressible promoter include e.g., the native pAOX1 or pAOX2 and functional variants thereof, any of the regulatory promoter, such as pG1-pG8, and fragments thereof, published in WO2013050551; any of the regulatory promoter, such as pG1 and pG1-x, published in WO2017021541 A1.

Suitable promoter sequences for use with yeast host cells are described in Mattanovich et al. (Methods Mol. Biol. (2012) 824:329-58) and include glycolytic enzymes like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPGI), the 3-phosphoglycerate kinase promoter (PPGK), the glycerol aldehyde phosphate dehydrogenase promoter (pGAP), translation elongation factor promoter (PTEF), and the promoters of *P. pastoris* enolase 1 (PEN01), triose phosphate isomerase (PTPI), ribosomal subunit proteins (PRPS2, PRPS7, PRPS31, PRPL1), alcohol oxidase promoter (PAOX1, PAOX2) or variants thereof with modified characteristics, the formaldehyde dehydrogenase promoter (PFLD), isocitrate lyase promoter (PICL), alphaketoisocaproate decarboxylase promoter (PTHI), the promoters of heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-02-oxidoreductase (PFET3), high affinity iron permease (PFTR1), repressible alkaline phosphatase (PPH08), N-myristoyl transferase (PNMT1), pheromone response transcription factor (PMCM1), ubiquitin (PUB14), single-stranded DNA endonuclease (PRAD2), the promoter of the major ADP/ATP carrier of the mitochondrial inner membrane (PPET9) (WO2008/128701) and the formate dehydrogenase (FMD) promoter. The GAP promoter, AOX1 or AOX2 promoter or a promoter derived from GAP or AOX1 or AOX2 promoter is particularly preferred. AOX promoters can be induced by methanol and are repressed by glucose.

Further examples of suitable promoters include *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase (PGK), and the maltase gene promoter (MAL).

According to a specific aspect, the expression cassette is integrated within a chromosome of the host cell, or within a plasmid.

The expression cassette may be introduced into the host cell and integrated into the host cell genome as intrachromosomal element e.g., at a specific site of integration or randomly integrated, whereupon a high producer host cell line is selected. Alternatively, the expression cassette may be integrated within an extrachromosomal genetic element, such as a plasmid or YAC. According to a specific example, the expression cassette is introduced into the host cell by a vector, in particular an expression vector, which is introduced into the host cell by a suitable transfection technique. For this purpose, the POI encoding polynucleotide may be ligated into an expression vector.

A preferred yeast expression vector (which is preferably used for expression in yeast) is selected from the group consisting of plasmids derived from pPICZ, pGAPZ, pPIC9, pPICZalfa, pGAPZalfa, pPIC9K, pGAPHis or pPUZZLE.

Techniques for transfecting or transforming eukaryotic cells introducing a vector or plasmid are well known in the art. These can include lipid vesicle mediated uptake, heat shock mediated uptake, calcium phosphate mediated transfection (calcium phosphate/DNA co-precipitation), viral infection, and particularly using modified viruses such as, for example, modified adenoviruses, microinjection and electroporation.

According to a specific aspect, the host cell described herein may undergo one or more further genetic modifications e.g., for improving protein production.

Specifically, the host cell is further engineered to modify one or more genes influencing proteolytic activity used to generate protease deficient strains, in particular a strain deficient in carboxypeptidase Y activity. Particular examples are described in WO1992017595A1. Further examples of a protease deficient *Pichia* strain with a functional deficiency in a vacuolar protease, such as proteinase A or proteinase B, are described in U.S. Pat. No. 6,153,424A. Further examples are *Pichia* strains which have an ade2 deletion, and/or deletions of one or both of the protease genes, PEP4 and PRB1, are provided by e.g., Thermo Fisher Scientific.

Specifically, the host cell is engineered to modify at least one nucleic acid sequence encoding a functional gene product, in particular a protease, selected from the group consisting of PEP4, PRB1, YPS1, YPS2, YMP1, YMP2, YMP1, DAP2, GRHI, PRD1, YSP3, and PRB3, as disclosed in WO2010099195A1.

The POI can be any one of eukaryotic, prokaryotic or synthetic peptides, polypeptides, proteins, or metabolites of a host cell.

Specifically, the POI is heterologous to the host cell species.

Specifically, the POI is a secreted peptide, polypeptide, or protein, i.e. secreted from the host cell into the cell culture supernatant.

Specifically, the POI is a eukaryotic protein, preferably a mammalian derived or related protein such as a human protein or a protein comprising a human protein sequence, or a bacterial protein or bacterial derived protein.

Preferably, the POI is a therapeutic protein functioning in mammals.

In specific cases, the POI is a multimeric protein, specifically a dimer or tetramer.

According to a specific aspect, the POI is a peptide or protein selected from the group consisting of an antigen-binding protein, a therapeutic protein, an enzyme, a peptide, a protein antibiotic, a toxin fusion protein, a carbohydrate—protein conjugate, a structural protein, a regulatory protein, a vaccine antigen, a growth factor, a hormone, a cytokine, a process enzyme, and a metabolic enzyme.

A specific POI is an antigen-binding molecule such as an antibody, or a fragment thereof, in particular an antibody fragment comprising an antigen-binding domain. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH, VHH, IgNARs, or V-NAR, or any protein comprising an immunoglobulin-fold domain. Further antigen-binding molecules may be selected from antibody mimetics, or (alternative) scaffold proteins such as e.g., engineered Kunitz domains, Adnectins, Affibodies, Affiline, Anticalins, or DARPins.

According to a specific aspect, the POI is e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin deternir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AID-SVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131 I-TM-601, KK-220, T-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, or TP-9201, adalimumab (HUMIRA), infliximab (REMICADE™), rituximab (RITUXAN™/MAB THERA™), etanercept (ENBREL™) bevacizumab (AVASTIN™), trastuzumab (HERCEPTIN™), pegrilgrastim (NEULASTA™), or any other suitable POI including biosimilars and biobetters.

According to a specific aspect, the host cell can be any animal cell, a vertebrate cell, a mammalian cell, a human cell, a plant cell, a nematodal cell, an invertebrate cell such as an insect cell or a mollusc cell, a stem cell derived of any of the foregoing, or a fungal cell or a yeast cell. Specifically the host cell is a cell of a genus selected from the group consisting of *Pichia, Hansenula, Komagataella, Saccharomyces, Kluyveromyces, Candida, Ogataea, Yarrowia*, and *Geotrichum*, specifically *Saccharomyces cerevisiae, Pichia pastoris, Ogataea minuta* or *Hansenula polymorpha*, or of filamentous fungi like *Aspergillus awamori* or *Trichoderma reesei*. Preferably, the host cell is a methylotrophic yeast, preferably *Pichia pastoris*. Herein *Pichia pastoris* is used synonymously for all, *Komagataella pastoris, Komagataella phaffii* and *Komagataella pseudopastoris*.

According to a specific aspect, the host cell is a yeast or filamentous fungal cell selected from the group consisting of *Pichia pastoris, Hansenula polymorpha, Trichoderma reesei, Saccharomyces cerevisiae, Kluyveromyces lactis, Yarrowia lipolytica, Pichia methanolica, Candida boidinii, Komagataella phaffii, Komagataella pastoris* and *Schizosaccharomyces pombe*.

According to a specific aspect, the host cell is a lower eukaryotic cell such as e.g. a yeast cell (e.g., *Pichia* genus (e.g. *Pichia pastoris, Pichia methanolica, Pichia kluyveri,* and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii*), the *Geotrichum* genus (e.g. *Geotrichum fermentans*), *Hansenula polymorpha, Yarrowia lipolytica,* or *Schizosaccharomyces pombe*. Preferred is the species *Pichia pastoris*. Examples for *Pichia pastoris* strains are X33, GS115, KM71, KM71H; CBS 2612, and CBS7435.

Specifically, the host cell is a *Pichia pastoris* strain selected from the group consisting of CBS 704, CBS 2612, CBS 7435, CBS 9173-9189, DSMZ 70877, X-33, GS115, KM71, KM71H and SMD1168.

Sources: CBS 704 (=NRRL Y-1603=DSMZ 70382), CBS 2612 (=NRRL Y-7556), CBS 7435 (=NRRL Y-11430), CBS 9173-9189: CBS-KNAW Fungal Biodiversity Centre, Centraalbureau voor Schimmelculturen, Utrecht, The Netherlands), and DSMZ 70877 (German Collection of Microorganisms and Cell Cultures); strains from Invitrogen, such as X-33, GS115, KM71, KM71H and SMD1168. Examples of *S. cerevisiae* strains include W303, CEN.PK and the BY-series (EUROSCARF collection). All of the strains described above have been successfully used to produce transformants and express heterologous genes.

The eukaryotic host cell can be a fungal cell (e.g., *Aspergillus* (such as *A. niger, A. fumigatus, A. oryzae, A. nidulans*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. oryzae*), *Myceliophthora* (such as *M. thermophile*), *Nectria* (such as *N. haematococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

According to a specific aspect, the mammalian cell is a human or rodent or bovine cell, cell line or cell strain. Examples of specific mammalian cells suitable as host cells described herein are mouse myeloma (NSO)-cell lines, Chinese hamster ovary (CHO)-cell lines, HT1080, H9, HepG2, MCF7, MDBK Jurkat, MDCK, NIH3T3, PC12, BHK (baby hamster kidney cell), VERO, SP2/0, YB2/0, Y0, C127, L cell, COS, e.g., COS1 and COS7, QC1-3, HEK-293, VERO, PER.C6, HeLA, EBI, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a DUKX CHO cell, a CHO—S, a CHO FUT8 knock-out CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells also include avian cells, cell lines or cell strains, such as for example, EBx® cells, EB14, EB24, EB26, EB66, or EBvl3.

According to another specific aspect, the eukaryotic cell is an insect cell (e.g., Sf9, Mimic Sf9, Sf21, High Five™ (BT1-TN-5B1-4), or BT1-Ea88 cells), an algae cell (e.g., of the genus Amphora, Bacillariophyceae, *Dunaliella, Chlorella, Chlamydomonas,* Cyanophyta (cyanobacteria), *Nannochloropsis, Spirulina,* or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

According to a specific embodiment, the invention provides for a method for producing a protein of interest (POI) in a eukaryotic host cell, comprising the steps:
i) genetically modifying the host cell to reduce production of at least one endogenous host cell protein (HCP) selected from the group consisting of a first HCP (HCP1), a second HCP (HCP2), and a third HCP (HCP3), wherein
   a) HCP1 comprises the amino acid sequence identified as SEQ ID NO:1, if the host cell is *Komagataella phaffii*, or its homologous sequence that is endogenous to the host cell if of another species;

b) HCP2 comprises the amino acid sequence identified as SEQ ID NO:3, if the host cell is *Komagataella phaffii*, or its homologous sequence that is endogenous to the host cell if of another species; and c) HCP3 comprises the amino acid sequence identified as SEQ ID NO:5, if the host cell is *Komagataella phaffii*, or its homologous sequence that is endogenous to the host cell if of another species.

ii) introducing into the host cell an expression cassette comprising one or more regulatory nucleic acid sequences operably linked to a nucleotide sequence encoding the POI;

iii) culturing said host cell under conditions to produce said POI; and optionally;

iv) isolating said POI from the cell culture, in particular from the cell culture supernatant; and optionally v) purifying said POI.

Specifically, the POI interest can be produced by culturing the host cell in an appropriate medium, isolating the expressed POI from the culture, in particular the cell culture supernatant and purifying it by a method appropriate for the expressed product, in particular to separate the POI from the cell. Thereby, a purified POI preparation can be produced.

According to a further specific embodiment, the invention provides for a method for producing a eukaryotic host cell capable of producing a protein of interest (POI) in a host cell culture, by introducing Specifically, step i) of the method described herein is carried out before, or after, or concomitantly with step ii).

According to a specific aspect, the host cell is first genetically modified to reduce said at least one HCP before being engineered for producing the heterologous or recombinant POI. According to a specific example, a wild-type host cell is genetically modified according to step i) of the method described herein. Specifically, the host cell is provided upon introducing said one or more genetic modifications for HCP reduction into a wild-type host cell strain.

According to a further aspect, the host cell is first engineered for producing the heterologous or recombinant POI, before being further genetically modified to reduce said at least one HCP. According to a specific example, a wild-type host cell may first be engineered to comprise the expression cassette for POI production. Such engineered host cell may then be further modified to reduce the HCP as further described herein.

According to a further aspect, the host cell is undergoing both, the engineering for POI production and genetically modifying for HCP reduction in one method step, e.g., employing the respective expression cassette, reagents and tools in one or more reaction mixtures.

Specifically, the host cell is a cell line cultured in a cell culture, in particular a production host cell line.

According to a further specific embodiment, the invention provides for a method for producing a protein of interest (POI) by culturing the host cell described herein, or obtainable by a method described herein, under conditions to produce said POI.

According to a further specific embodiment, the invention provides for the use of the host cell described herein for the production of a POI.

According to a specific embodiment, the cell line is cultured under batch, fed-batch or continuous culture conditions. The culture may be performed in microtiter plates, shake-flasks, or a bioreactor starting with a batch phase as the first step, followed by a fed-batch phase or a continuous culture phase as the second step.

Specifically, the method described herein comprises at least one genetic modification of the host cell to reduce the amount of said at least one HCP as further described herein. In particular, the at least one genetic modification introduces any one or more of the following features of HCP reduction in the host cell compared to the host cell without said genetic modification for HCP reduction, in particular when culturing under conditions to express said POI:

the amount of said at least one HCP produced by the host cell is reduced to less than any one of 10%, 5%, or 3% (mol/mol) of total HCP;

the amount of said at least one HCP produced by the host cell is reduced by at least any one of 50%, 60%, 70%, 80%, 90%, 95%, (mol/mol), or even by 100%, thereby abolishing production of the respective HCP;

the amount of each of said at least one HCP produced by the host cell, in particular each of HCP1 and any one, two, or three of HCP2, HCP3, or HCP4, is reduced by at least any one of 50%, 60%, 70%, 80%, 90%, 95%, or 100% (mol/mol);

the amount of each of said at least one HCP produced by the host cell, in particular each of HCP1 and any one, two, or three of HCP2, HCP3, or HCP4, is reduced to less than 1% mol/mol) of total HCP;

the amount of total HCP in the cell culture supernatant is reduced by at least any of 5%, or 10%, or 15% (mol/mol).

According to a further specific embodiment, the invention provides for a method of reducing the risk of endogenous host cell protein (HCP) contaminations of a protein of interest (POI) produced in a host cell culture, by culturing the host cell described herein under conditions to produce said POI and isolating the POI from said cell culture. By reducing the amount of HCP, the purity of the POI in the host cell culture, or a fraction thereof can be effectively increased.

FIGURES

FIG. 1: HCP Sequences described herein

HCP1 of *Komagataella phaffii*

SEQ ID NO:1: amino acid sequence of F2QXM5 (NCBI accession number): Uncharacterized protein, PP7435_Chr3-1213, PAS_Chr3_0030, gi I 254570259, gi I 328353755, P1PA05357, CCA40153;

SEQ ID NO:2: nucleotide sequence corresponding to F2QXM5 (NCBI accession number): Uncharacterized protein, PP7435_Chr3-1213, PAS_Chr3_0030, gi I 254570259, gi 1328353755, PIPA05357, CCA40153;

HCP2 of *Komagataella phaffii*

SEQ ID NO:3: amino acid sequence of F2QNG1 (NCBI accession number): Cell wall protein with similarity to glucanases, PP7435_Chr1-0232, PAS_Chr1-3_0229, gi I 25456492, gi 1328349994, P1PA04722;

SEQ ID NO:4: nucleotide sequence corresponding to F2QNG1 (NCBI accession number): Cell wall protein with similarity to glucanases, PP7435_Chr1-0232, PAS_Chr1-3_0229, gi 125456492, gi 1328349994, PIPA04722;

HCP3 of *Komagataella phaffii*

SEQ ID NO:5: amino acid sequence of F2QQT7 (NCBI accession number): Protein of the SUN family (Sim1p, Uth1p, Nca3p, Sun4p), PAS_chr2-2_0064;

SEQ ID NO:6: nucleotide sequence corresponding to F2QQT7: Protein of the SUN family (Sim1p, Uth1p, Nca3p, Sun4p), PAS_chr2-2_0064;

HCP4 of *Komagataella phaffii*
  SEQ ID NO:7: amino acid sequence of F2QXH5 (NCBI accession number): EPX1; Extracellular protein X1, PAS_chr3_0076, PIPA00934, PP7435_Chr3-1160;
  SEQ ID NO:8: nucleotide sequence corresponding to F2QXH5 (NCBI accession number): EPX1; Extracellular protein X1, PAS_chr3_0076, PIPA00934, PP7435_Chr3-1160;
HCP1 Homolog of *Komagataella pastoris*
  SEQ ID NO:20: amino acid sequence of NCBI accession number: BA75_00021T0 [*Komagataella pastoris*], GenBank: ANZ74151.1;
HCP2 Homolog of *Komagataella pastoris*
  SEQ ID NO:21: amino acid sequence of NCBI accession number: BA75_01624T0 [*Komagataella pastoris*], GenBank: ANZ73790.1;
HCP3 Homolog of *Komagataella pastoris*
  SEQ ID NO:22: amino acid sequence of NCBI accession number: BA75_01931T0 [*Komagataella pastoris*], GenBank: ANZ76017.1;
HCP4 Homolog of *Komagataella pastoris*
  SEQ ID NO:23: amino acid sequence of NCBI accession number: BA75_00070T0 [*Komagataella pastoris*]; GenBank: ANZ73364.1;
HCP2 Homolog of *S. cerevisiae*
  SEQ ID NO:24: amino acid sequence of NCBI accession number: SCW10 [*Saccharomyces cerevisiae*], Gen Bank: KZVO9161.1; >SCW10 YMR305C SGDID: S000004921;
HCP2 Homolog of *S. cerevisiae*
  SEQ ID NO:25: amino acid sequence of NCBI accession number: SCW4 [*Saccharomyces cerevisiae*], GenBank: KZV11513.1; >SCW4 YGR279C SGDID: S000003511;
HCP3 Homolog of *S. cerevisiae*
  SEQ ID NO:26: amino acid sequence of NCBI accession number: SUN4 [*Saccharomyces cerevisiae*]; GenBank: CAA95939.1; >SUN4 YNL066W SGDID: S000005010.

FIG. 2: PCR-based verification of the HCP1 knock-out strains. The gene encoding for HCP1 was partially deleted using the split-marker-cassette system in the CBS2612 wild type strain, as well as in three strains expressing each one of the three proteins of interest (POI1-3). A verification PCR using the primer pair Control_Forward and Control_Reverse gives a PCR product of 4602 bp in case of a HCP1 knock-out, compared to 3699 bp when the genomic locus is still intact. Two restriction digests on the PCR products were performed with either EcoRI or NcoI to additionally verify the PCR amplicon. The PCR product of the positive knock-out strains is not cleaved by EcoRI (4602 bp fragment); while it is digested by NcoI (1955 bp and 2647 bp fragments). For all knock-out strains, the successful deletion could be confirmed.

Figure 3:
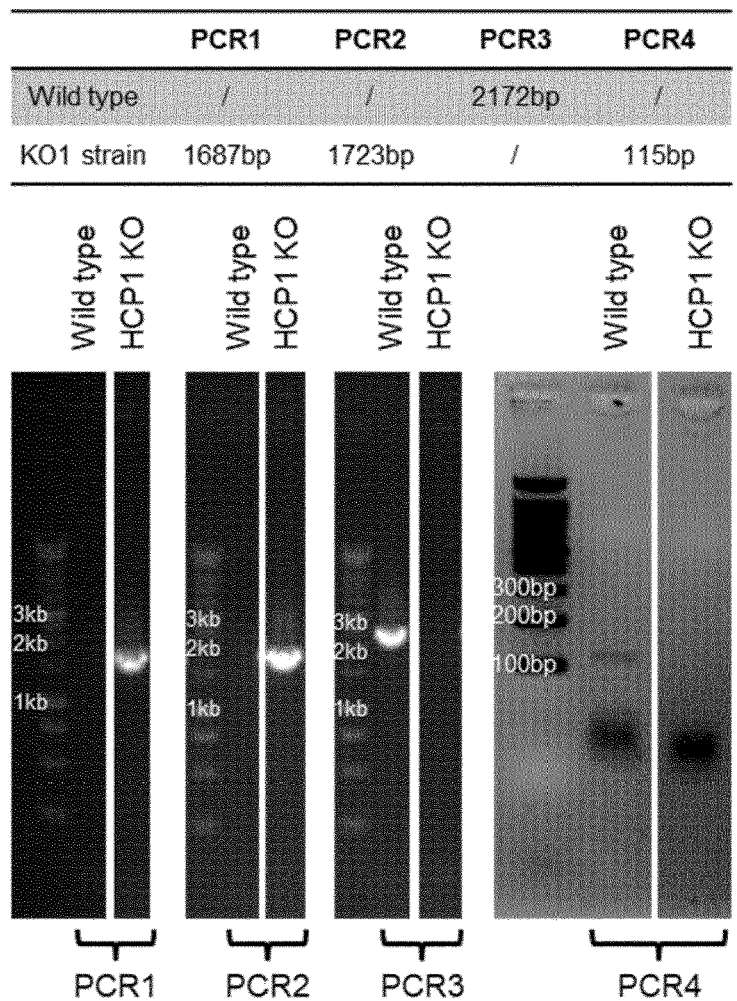

FIG. 3: PCR-based verification of the background HCP1 KO strain.

Figure 4:
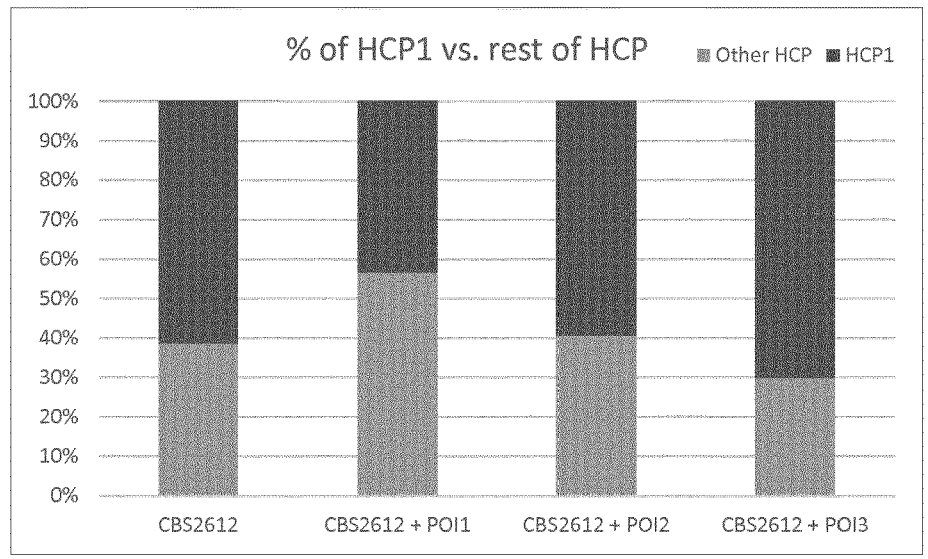

FIG. 4: Graphical representation of the abundance of HCP1 compared to all the other HCP in wild type *Pichia* (CBS2612) and wild type *Pichia* strains expressing any of the three POIs. HCP1 accounts for an astounding 43-70% of the total HCP content in end of fermentation samples.

Figure 5:
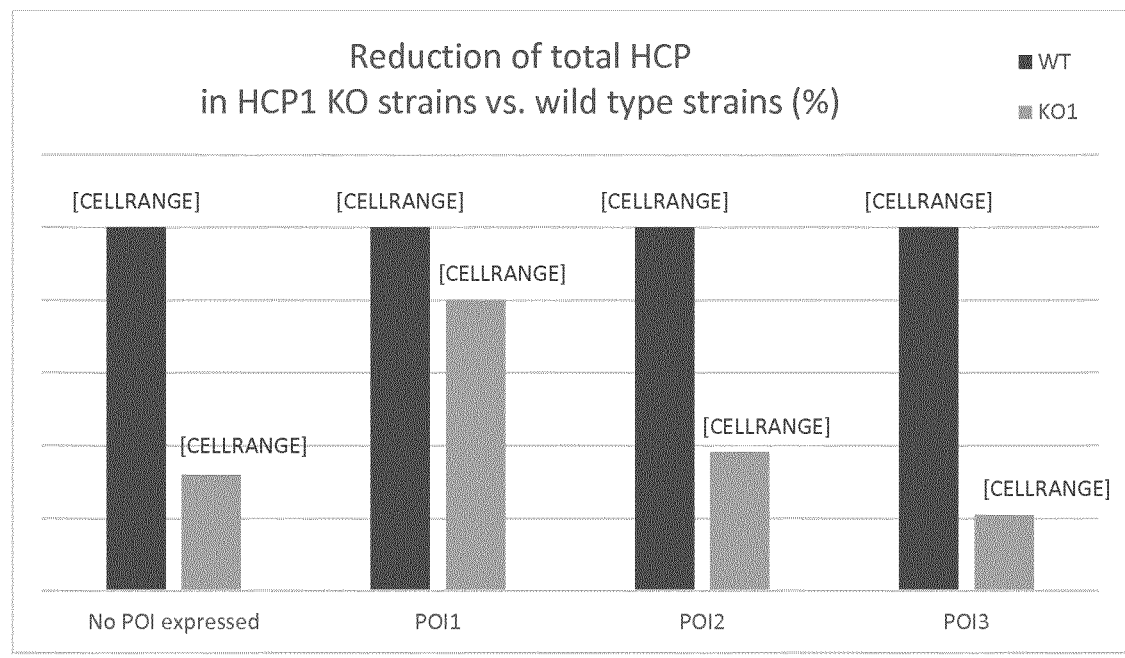

FIG. 5: 20-79% reduction of total HCP in HCP1 KO strains compared to wild type strains.

DETAILED DESCRIPTION OF THE INVENTION

Specific terms as used throughout the specification have the following meaning.

The term "host cell" as used herein shall refer to a single cell, a single cell clone, or a cell line of a host cell.

The term "cell line" as used herein refers to an established clone of a particular cell type that has acquired the ability to proliferate over a prolonged period of time. A cell line is typically used for expressing an endogenous or recombinant gene, or products of a metabolic pathway to produce polypeptides or cell metabolites mediated by such polypeptides. A "production host cell line" or "production cell line" is commonly understood to be a cell line ready-to-use for cell culture in a bioreactor to obtain the product of a production process, such as a POI.

The host cell producing the POI as described herein is also referred to as "production host cell", and a respective cell line a "production cell line".

Specific embodiments described herein refer to a production host cell line which is characterized by a low HCP expression.

The term "eukaryotic host cell" shall mean any eukaryotic cell or organism, which may be cultured to produce a POI or a host cell metabolite. It is well understood that the term does not include human beings.

The term "cell culture" as used herein with respect to a host cell refers to the maintenance of cells in an artificial, e.g., an in vitro environment, under conditions favoring growth, differentiation or continued viability, in an active or quiescent state, of the cells, specifically in a controlled bioreactor according to methods known in the industry.

When culturing a cell culture using appropriate culture media, the cells are brought into contact with the media in a culture vessel or with substrate under conditions suitable to support culturing the cells in the cell culture. As described herein, a culture medium is provided that can be used for the growth of eukaryotic cells, specifically yeast or filamentous fungi. Standard cell culture techniques are well-known in the art.

The cell cultures as described herein particularly employ techniques which provide for the production of a secreted POI, such as to obtain the POI in the cell culture medium, which is separable from the cellular biomass, herein referred to as "cell culture supernatant", and may be purified to obtain the POI at a higher degree of purity. When a protein (such as e.g., a HCP or a POI) is produced and secreted by the host cell in a cell culture, it is herein understood that such proteins are secreted into the cell culture supernatant, and can be obtained by separating the cell culture supernatant from the host cell biomass, and optionally further purifying the protein to produce a purified protein preparation.

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations. Feeding of nutrients may be done in a continuous or discontinuous mode according to methods known in the art.

Whereas a batch process is a cell culture mode in which all the nutrients necessary for culturing the cells are contained in the initial culture medium, without additional supply of further nutrients during fermentation, in a fed-batch process, after a batch phase, a feeding phase takes place in which one or more nutrients are supplied to the culture by feeding. Although in most processes the mode of feeding is critical and important, the host cell and methods described herein are not restricted with regard to a certain mode of cell culture.

In certain embodiments, the cell culture process is a fed-batch process. Specifically, a host cell transformed with a nucleic acid construct encoding a desired recombinant POI, is cultured in a growth phase and transitioned to a production phase in order to produce a desired recombinant POI.

In another embodiment, host cells described herein are cultured in a continuous mode, e.g., a chemostat. A continuous fermentation process is characterized by a defined, constant and continuous rate of feeding of fresh culture medium into a bioreactor, whereby culture broth is at the same time removed from the bioreactor at the same defined, constant and continuous removal rate. By keeping culture medium, feeding rate and removal rate at the same constant level, the cell culture parameters and conditions in the bioreactor remain constant.

A recombinant POI can be produced using the host cell and the respective cell line described herein, by culturing in an appropriate medium, isolating the expressed product or metabolite from the culture, and optionally purifying it by a suitable method.

Several different approaches for the production of the POI as described herein are preferred. A POI may be expressed, processed and optionally secreted by transforming a eukaryotic host cell with an expression vector harboring recombinant DNA encoding the relevant protein, preparing a culture of the transformed cell, growing the culture, inducing transcription and POI production, and recovering the POI.

The term "host cell protein", abbreviated "HCP", as used herein refers to individual secreted proteins produced by host cells. If host cells are expressing a POI, HCP is understood as a byproduct of the POI. Therefore the POI is not understood as a HCP. HCP is typically present in the cell culture medium or cell culture supernatant once cells are separated from the cell culture media by e.g. centrifugation. The sum of all HCPs is referred to as "total HCP". There is a risk that HCPs are contaminating a preparation of host cell products, e.g. including a POI, or a POI preparation. Current analytical methods to assay for the presence of contaminant HCPs in POI products include ELISA, HPLC, capillary electrophoresis, SDS-PAGE, or mass spectrometry, in particular wherein mass spectrometry is liquid chromatography-mass spectrometry (LC-MS), or, preferably liquid chromatography tandem-mass spectrometry (LC-MS/MS), e.g., as known in the art, and/or further described in the Examples section.

The host cell described herein is typically tested for its expression capacity, HCP content or POI yield by any of the following tests: ELISA, activity assay, HPLC, or other suitable tests, such as SDS-PAGE and Western Blotting Techniques, or mass spectrometry.

To determine the effect of a genetic modification on the reduction of HCP in the cell culture and e.g., on the amount of impurities in a POI so produced, the host cell line may be cultured in microtiter plates, shake flask, or bioreactor using fedbatch or chemostat fermentations in comparison with strains without such genetic modification in the respective cell.

The production method described herein specifically allows for the fermentation on a pilot or industrial scale. The industrial process scale would preferably employ volumes of at least 10 L, specifically at least 50 L, preferably at least 1 $m^3$, preferably at least 10 $m^3$, most preferably at least 100 $m^3$.

Production conditions in industrial scale are preferred, which refer to e.g., fed batch culture in reactor volumes of 100 L to 10 $m^3$ or larger, employing typical process times of several days, or continuous processes in fermenter volumes of approximately 50-1000 L or larger, with dilution rates of approximately 0.02-0.15 $h^{-1}$.

The devices, facilities and methods used for the purpose described herein are specifically suitable for use in and with culturing any desired cell line including prokaryotic and/or eukaryotic cell lines. Further, in embodiments, the devices, facilities and methods are suitable for culturing any cell type including suspension cells or anchorage-dependent (adherent) cells and are suitable for production operations configured for production of pharmaceutical and biopharmaceutical products—such as polypeptide products (POI), nucleic acid products (for example DNA or RNA), or cells and/or viruses such as those used in cellular and/or viral therapies.

In embodiments, the cells express or produce a product, such as a recombinant therapeutic or diagnostic product. As described in more detail herein, examples of products produced by cells include, but are not limited to, POIs such as exemplified herein including antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), or viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., POIs including proteins, peptides, or antibiotics, amino acids, nucleic acids (such as DNA or RNA), synthesized by said cells in a large-scale manner. Unless stated otherwise herein, the devices, facilities, and methods can include any desired volume or production capacity including but not limited to bench-scale, pilot-scale, and full production scale capacities.

Moreover, and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally, and unless otherwise stated, the devices, systems, and methods described herein can be housed and/or performed in a single location or facility or alternatively be housed and/or performed at separate or multiple locations and/or facilities.

Suitable techniques may encompass culturing in a bioreactor starting with a batch phase, followed by a short exponential fed batch phase at high specific growth rate, further followed by a fed batch phase at a low specific growth rate. Another suitable culture technique may encompass a batch phase followed by a fed-batch phase at any suitable specific growth rate or combinations of specific growth rate such as going from high to low growth rate over POI production time, or from low to high growth rate over POI production time. Another suitable culture technique may encompass a batch phase followed by a continuous culturing phase at a low dilution rate.

A preferred embodiment includes a batch culture to provide biomass followed by a fed-batch culture for high yields POI production.

It is preferred to culture a host cell as described herein in a bioreactor under growth conditions to obtain a cell density of at least 1 g/L cell dry weight, more preferably at least 10 g/L cell dry weight, preferably at least 20 g/L cell dry weight, preferably at least any one of 30, 40, 50, 60, 70, or 80 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH_4)_2SO_4$;

Preferred sulphur sources include $MgSO_4$, or $(NH_4)_2SO_4$ or $K_2SO_4$;

Preferred phosphate sources include $NH_4H_2PO_4$, or $H_3PO_4$ or $NaH_2PO_4$, $KH_2PO_4$, $Na_2HPO_4$ or $K_2HPO_4$;

Further typical medium components include KCl, $CaCl_2$, and Trace elements such as: Fe, Co, Cu, Ni, Zn, Mo, Mn, I, B;

Preferably the medium is supplemented with vitamin $B_7$;

A typical growth medium for *P. pastoris* comprises glycerol, sorbitol or glucose, $NH_4H_2PO_4$, $MgSO_4$, KCl, $CaCl_2$, biotin, and trace elements.

In the production phase a production medium is specifically used with only a limited amount of a supplemental carbon source.

Preferably the host cell line is cultured in a mineral medium with a suitable carbon source, thereby further simplifying the isolation process significantly. An example of a preferred mineral medium is one containing an utilizable carbon source (e.g., glucose, glycerol, sorbitol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g., to complement auxotrophies.

Specifically, the cells are cultured under conditions suitable to effect expression of the desired POI, which can be purified from the cells or culture medium, depending on the nature of the expression system and the expressed protein, e.g., whether the protein is fused to a signal peptide and whether the protein is soluble or membrane-bound. As will be understood by the skilled artisan, culture conditions will vary according to factors that include the type of host cell and particular expression vector employed.

A typical production medium comprises a supplemental carbon source, and further $NH_4H_2PO_4$, $MgSO_4$, KCl, $CaCl_2$, biotin, and trace elements.

For example the feed of the supplemental carbon source added to the fermentation may comprise a carbon source with up to 50 wt % utilizable sugars.

The fermentation preferably is carried out at a pH ranging from 3 to 8.

Typical fermentation times are about 24 to 120 hours with temperatures in the range of 20° C. to 35° C., preferably 22-30° C.

The POI is preferably expressed employing conditions to produce yields of at least 1 mg/L, preferably at least 10 mg/L, preferably at least 100 mg/L, most preferred at least 1 g/L.

The term "expression" or "expression cassette" as used herein refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into a host chromosome. Expression may refer to secreted or non-secreted expression products, including polypeptides or metabolites.

Expression cassettes are conveniently provided as expression constructs e.g., in the form of "vectors" or "plasmids", which are typically DNA sequences that are required for the transcription of cloned recombinant nucleotide sequences, i.e. of recombinant genes and the translation of their mRNA in a suitable host organism. Expression vectors or plasmids usually comprise an origin for autonomous replication in the host cells, selectable markers (e.g., an amino acid synthesis gene or a gene conferring resistance to antibiotics such as zeocin, kanamycin, G418 or hygromycin, nourseothricin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences, such as artificial chromosomes e.g., a yeast artificial chromosome (YAC).

Expression vectors may include but are not limited to cloning vectors, modified cloning vectors and specifically designed plasmids. Preferred expression vectors described herein are expression vectors suitable for expressing of a recombinant gene in a eukaryotic host cell and are selected depending on the host organism. Appropriate expression vectors typically comprise regulatory sequences suitable for expressing DNA encoding a POI in a eukaryotic host cell. Examples of regulatory sequences include operators, enhancers, ribosomal binding sites, and sequences that control transcription and translation initiation and termination. The regulatory sequences may be operably linked to the DNA sequence to be expressed.

To allow expression of a recombinant nucleotide sequence in a host cell, the expression vector may provide a promoter adjacent to the 5' end of the coding sequence, e.g., upstream from a gene of interest (GOI) or a signal peptide gene enabling secretion of the POI. The transcription is thereby regulated and initiated by this promoter sequence.

The expression construct described herein specifically comprises a promoter operably linked to a nucleotide sequence encoding a POI under the transcriptional control of said promoter. Specifically, the promoter is not natively associated with the coding sequence of the POI.

Also multicloning vectors, which are vectors having a multicloning site, can be used as described herein, wherein a desired heterologous gene can be incorporated at a multicloning site to provide an expression vector. In the case of multicloning vectors, because the gene of the POI is introduced at the multicloning site, a promoter is typically placed upstream of the multicloning site.

The term "endogenous" as used herein is meant to include those molecules and sequences, in particular endogenous proteins, which are present in the wild-type (native) host cell, prior to its modification to reduce the endogenous proteins. In particular, an endogenous nucleic acid molecule (e.g., a gene) or protein that does occur in (and can be obtained from) a particular host cell as it is found in nature, is understood to be "host cell endogenous" or "endogenous to the host cell". Moreover, a cell "endogenously expressing" a nucleic acid or protein expresses that nucleic acid or protein as does a host of the same particular type as it is found in nature. Moreover, a host cell "endogenously producing" or that "endogenously produces" a nucleic acid, protein, or other compound produces that nucleic acid, protein, or compound as does a host cell of the same particular type as it is found in nature.

Thus, even if an endogenous protein is no more produced by a host cell, such as in a knockout mutant of the host cell, where the protein encoding gene is inactivated or deleted, the protein is herein still referred to as "endogenous".

The term "heterologous" as used herein with respect to a nucleotide or amino acid sequence or protein, refers to a compound which is either foreign, i.e. "exogenous", such as not found in nature, to a given host cell; or that is naturally found in a given host cell, e.g., is "endogenous", however, in the context of a heterologous construct, e.g., employing a heterologous nucleic acid. The heterologous nucleotide sequence as found endogenously may also be produced in an unnatural, e.g., greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with a promoter, e.g., to obtain a hybrid promoter, or operably linked to a coding sequence, as described herein. As a result, a hybrid or chimeric polynucleotide may be obtained. A further example of a heterologous compound is a POI encoding polynucleotide operably linked to a transcriptional control element, e.g., a promoter, to which an endogenous, naturally-occurring POI coding sequence is not normally operably linked.

The term "host cell" as described herein specifically refers to an artificial organism and a derivative of a native (wild-type) host cell. It is well understood that the host cells, methods and uses described herein, e.g., specifically referring to one or more genetic modifications, expression constructs, transformed host cells and recombinant proteins, are non-naturally occurring, "man-made" or synthetic, and are therefore not considered as a result of "law of nature".

The host cell is specifically a recombinant host cell engineered to reduce the amount of the host cell's endogenous HCP which is produced by the cell and obtained in the cell culture supernatant. Specifically one or more proteins which are abundant in the culture of the wild-type host cell are the target of genetic modification to reduce their expression. A protein is specifically considered to be abundant, if it is present in the cell culture supernatant at a high level, e.g., if it amounts to at least 10%, or at least 5% (mol/mol) of the total HCP. According to specific embodiments, the host cell is engineered to knock-down or knockout (for inactivation or deletion of a gene or a part thereof) the host cell genes encoding at least one, two, or three of the most abundantly secreted endogenous proteins.

Specifically, a deletion strain is provided, wherein a gene is disrupted.

The term "disrupt" as used herein refers to the significant reduction to complete removal of the expression of one or more endogenous proteins in a host cell, such as be knock-down or knockout. This may be measured as presence of this one or more endogenous proteins in a culture medium of the host cell, such as by mass spectrometry wherein the total content of a endogenous protein may be less than a threshold or non-detectable.

The term "disrupted" specifically refers to a result of genetic engineering by at least one step selected from the group consisting of gene silencing, gene knock-down, gene knockout, delivery of a dominant negative construct, conditional gene knock-out, and/or by gene alteration with respect to a specific gene.

The term "knock-down", "reduction" or "depletion" in the context of gene expression as used herein refers to experimental approaches leading to reduced expression of a given gene compared to expression in a control cell. Knock-down of a gene can be achieved by various experimental means such as introducing nucleic acid molecules into the cell which hybridize with parts of the gene's mRNA leading to its degradation (e.g., shRNAs, RNAi, miRNAs) or altering the sequence of the gene in a way that leads to reduced transcription, reduced mRNA stability or diminished mRNA translation.

A complete inhibition of expression of a given gene is referred to as "knockout". Knockout of a gene means that no functional transcripts are synthesized from said gene leading to a loss of function normally provided by this gene. Gene knockout is achieved by altering the DNA sequence leading to disruption or deletion of the gene or its regulatory sequences, or part of such gene or regulatory sequences. Knockout technologies include the use of homologous recombination techniques to replace, interrupt or delete crucial parts or the entire gene sequence or the use of DNA-modifying enzymes such as zinc-finger or meganucleases to introduce double strand breaks into DNA of the target gene e.g., described by Gaj et al. (Trends Biotechnol. 2013; 31(7):397-405).

Specific embodiments employ one or more knockout plasmids which are transfected into the host cells. By homologous recombination the target gene in the host cells can be disrupted. This procedure is typically repeated until all alleles of the target gene are stably removed.

One specific method for knocking out a specific gene as described herein is the CRISPR-Cas9 methods as described in e.g., Weninger et al. (J. Biotechnol. 2016, 235:139-49).

Another embodiment refers to target mRNA degradation by using small interfering RNA (siRNA) to transfect the host cell and targeting a mRNA encoding the target protein contaminant expressed endogenously by said host cell.

The term "gene expression", as used herein, is meant to encompass at least one step selected from the group consisting of DNA transcription into mRNA, mRNA processing, non-coding mRNA maturation, mRNA export, translation, protein folding and/or protein transport.

Gene expression of a gene may be inhibited or reduced by methods which directly interfere with gene expression, encompassing, but not restricted to, inhibition or reduction of DNA transcription, e.g., by use of specific promoter-related repressors, by site specific mutagenesis of a given promoter, by promoter exchange, or inhibition or reduction of translation, e.g., by RNAi induced post-transcriptional gene silencing. The expression of a dysfunctional or inactive gene product with reduced activity, can, for example, be achieved by site specific or random mutagenesis, insertions or deletions within the coding gene.

The inhibition or reduction of the activity of gene product can, for example, be achieved by administration of, or incubation with, an inhibitor to the respective enzyme, prior to or simultaneously with protein expression. Examples for such inhibitors include, but are not limited to, an inhibitory peptide, an antibody, an aptamer, a fusion protein or an antibody mimetic against said enzyme, or a ligand or receptor thereof, or an inhibitory peptide or nucleic acid, or a small molecule with similar binding activity. Other ways to inhibit the enzyme are the reduction of specific cofactors of the enzyme in the medium, like copper, which is a PAM specific ion cofactor (e.g., in the form of $CuSO_4$), ascorbate, which acts as an electron donor for PAM, molecular oxygen, catalase and others known today to the skilled artisan, or yet to be discovered in the future.

Gene silencing, gene knock-down and gene knockout refers to techniques by which the expression of a gene is reduced, either through genetic modification or by treatment with an oligonucleotide with a sequence complementary to either an mRNA transcript or a gene. If genetic modification of DNA is done, the result is a knock-down or knockout organism. If the change in gene expression is caused by an oligonucleotide binding to an mRNA or temporarily binding to a gene, this results in a temporary change in gene expression without modification of the chromosomal DNA and is referred to as a transient knock-down.

In a transient knock-down, which is also encompassed by the above term, the binding of this oligonucleotide to the active gene or its transcripts causes decreased expression through blocking of transcription (in the case of gene-binding), degradation of the mRNA transcript (e.g., by small interfering RNA (siRNA) or RNase-H dependent antisense) or blocking either mRNA translation, pre-mRNA splicing sites or nuclease cleavage sites used for maturation of other functional RNAs such as miRNA (e.g., by Morpholino oligos or other RNase-H independent antisense). Other approaches involve the use of shRNA (small hairpin RNA, which is a sequence of RNA that makes a tight hairpin turn that can be used to silence gene expression via RNA interference), esiRNA (Endoribonuclease-prepared siRNAs, which are a mixture of siRNA oligos resulting from cleavage of long double-stranded RNA (dsRNA) with an endoribonuclease), or the activation of the RNA-induced silencing complex (RISC).

Other approaches to carry out gene silencing, knock-down or knockout are known to the skilled person from the respective literature, and their application in the context of the present invention is considered as routine. Gene knockout refers to techniques by which the expression of a gene is fully blocked, i.e. the respective gene is inoperative, or even removed. Methodological approaches to achieve this goal are manifold and known to the skilled person. Examples are the production of a mutant which is dominantly negative for the given gene. Such mutant can be produced by site directed mutagenesis (e.g., deletion, partial deletion, insertion or nucleic acid substitution), by use of suitable transposons, or by other approaches which are known to the skilled person from the respective literature, the application of which in the context of the present invention is thus considered as routine. One example is knockout by use of targeted Zinc Finger Nucleases. A respective Kit is provided by Sigma Aldrich as "CompoZR knockout ZFN". Another approach encompasses the use of Transcription activator-like effector nucleases (TALENs).

The delivery of a dominant negative construct involves the introduction of a sequence coding for a dysfunctional enzyme, e.g., by transfection. Said coding sequence is functionally coupled to a strong promoter, in such way that the gene expression of the dysfunctional enzyme overrules the natural expression of the wild type enzyme, which, in turn, leads to an effective physiological defect of the respective enzyme activity.

A conditional gene knockout allows blocking gene expression in a tissue- or time-specific manner. This is done, for example, by introducing short sequences called loxP sites around the gene of interest. Again, other approaches are known to the skilled person from the respective literature, and their application in the context of the present invention is considered as routine.

One other approach is gene alteration which may lead to a dysfunctional gene product or to a gene product with reduced activity. This approach involves the introduction of frame shift mutations, nonsense mutations (i.e., introduction of a premature stop codon) or mutations which lead to an amino acid substitution which renders the whole gene product dysfunctional, or causing a reduced activity. Such gene alteration can for example be produced by mutagenesis (e.g., deletion, partial deletion, insertion or nucleic acid substitution), either unspecific (random) mutagenesis or site directed mutagenesis. Protocols describing the practical application of gene silencing, gene knock-down, gene knockout, delivery of a dominant negative construct, conditional gene knockout, and/or gene alteration are commonly available to the skilled artisan, and are within his routine. The technical teaching provided herein is thus entirely enabled with respect to all conceivable methods leading to an inhibition or reduction of gene expression of a gene product, or to the expression of a dysfunctional, or inactive gene product, or with reduced activity.

Genetic modifications described herein may employ tools, methods and techniques known in the art, such as described by J. Sambrook et al., Molecular Cloning: A Laboratory Manual (3rd edition), Cold Spring Harbor Laboratory, Cold Spring Harbor Laboratory Press, New York (2001).

The term "operably linked" as used herein refers to the association of nucleotide sequences on a single nucleic acid molecule, e.g., a vector, or an expression cassette, in a way such that the function of one or more nucleotide sequences is affected by at least one other nucleotide sequence present on said nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically, such nucleic acids operably linked to each other may be immediately linked, i.e. without further elements or nucleic acid sequences in between the nucleic acid encoding the signal peptide and the nucleic acid sequence encoding a POI.

A promoter sequence is typically understood to be operably linked to a coding sequence, if the promoter controls the transcription of the coding sequence. If a promoter sequence is not natively associated with the coding sequence, its transcription is either not controlled by the promoter in native (wild-type) cells or the sequences are recombined with different contiguous sequences.

The term "constitutive" with respect to regulatory element, such as a promoter shall refer to an element which is active in different cell culture conditions, using different media or substrates. Among the constitutive promoter of yeast cells, especially the GAP and the TEF promoters have been described to be strong, and useful for recombinant protein production.

A promoter is specifically understood as a constitutive promoter, if is capable of controlling expression without the need for induction, or the possibility of repression. Therefore, there is continuous and steady expression at a certain level. Preferably it has high promoter strength at all growth phases or growth rates of the host cell.

The term "regulatable" with respect to an inducible or repressible regulatory element, such as a promoter shall refer to an element that is repressed in a host cell in the presence of an excess amount of a substance (such as a nutrient in the cell culture medium) e.g., in the growth phase of a batch culture, and de-repressed to induce strong activity e.g., in the production phase (such as upon reducing the amount of a nutrient, or upon feeding of a supplemental substrate), according to a fed-batch strategy. A regulatory element can as well be designed to be regulatable, such that the element is inactive without addition of a cell culture additive, and active in the presence of such additive. Thus, expression of a POI under the control of such regulatory element can be induced upon addition of such additive.

The term "protein of interest (POI)" as used herein refers to a polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g., of the promoter sequence. In some cases the term POI as used herein also refers to any metabolite product by the host cell as mediated by the recombinantly expressed protein.

The term "scaffold" as used herein describes a multifaceted group of compact and stably folded proteins—differing in size, structure, and origin—that serve as a starting point for the generation of antigen-binding molecules. Inspired by the structure-function relationships of antibodies (immunoglobulins), such an alternative protein scaffold provides a robust, conserved structural framework that supports an interaction site which can be reshaped for the tight and specific recognition of a given (bio)molecular target.

The term "sequence identity" of a variant, homologue or orthologue as compared to a parent nucleotide or amino acid sequence indicates the degree of identity of two or more sequences. Two or more amino acid sequences may have the same or conserved amino acid residues at a corresponding position, to a certain degree, up to 100%. Two or more nucleotide sequences may have the same or conserved base pairs at a corresponding position, to a certain degree, up to 100%.

Sequence similarity searching is an effective and reliable strategy for identifying homologs with excess (e.g., at least 50%) sequence identity. Sequence similarity search tools frequently used are e.g., BLAST, FASTA, and HMMER.

Sequence similarity searches can identify such homologous proteins or genes by detecting excess similarity, and statistically significant similarity that reflects common ancestry. Homologues may encompass orthologues, which are herein understood as the same protein in different organisms, e.g., variants of such protein in different different organisms or species.

A homologous or orthologous sequence of the same protein in different organisms or species, specifically of the same genus, typically has at least about 50% sequence identity, preferably at least about 60% identity, more preferably at least about 70% identity, more preferably at least about 80% identity, more preferably at least about 90% identity, more preferably at least about 95% identity.

Each of the HCPs characterized by the sequences identified as SEQ ID NO:1-8 are of *K. phaffii*. It is well understood that there are homologous sequences present in other eukaryotic host cells. For example, yeast cells comprise the respective homologous sequences, in particular in yeast of *Pichia pastoris*, which has been reclassified into a new genus, *Komagataella*, and split into three species, *K. pastoris*, *K. phaffii*, and *K. pseudopastoris*. Further homologous sequences are e.g., found in *Saccharomyces cerevisiae* or *Yarrowia lipolytica*.

HCP1 (*K. phaffii*): F2QXM5: According to NCBI, the protein is Zonadhesin, belonging to the family of agglutinins, but blast analysis also displays limited homology to the subtilisin-like serine protease SUB2. In most databases, the protein is still designated as uncharacterized protein. 63 kDa, 587AAs.

The respective homologous sequence in *K. pastoris* is herein referred to as HCP1 homolog, characterized by an amino acid sequence comprising or consisting of SEQ ID NO:20 (NCBI accession number: BA75_00021 T0 [*Komagataella pastoris*], GenBank: ANZ74151.1).

HCP2 (*K. phaffii*): F2QNG1: SCW10, is a cell wall protein with similarity to glucanases. It is involved in carbohydrate metabolic processes and has hydrolase activity. The homologue in *Saccharomyces cerevisiae* may play a role in conjugation during mating.

The respective homologous sequence in *K. pastoris* is herein referred to as HCP2 homolog, characterized by an amino acid sequence comprising or consisting of SEQ ID NO:21 (NCBI accession number: BA75_01624 T0 [*Komagataella pastoris*], GenBank: ANZ73790.1).

HCP3 (*K. phaffii*): F2QQT7: SUN4, is another protein with similarity to glucanases. It is a protein of the SUN family (Sim1p,Uth1p,Nca3p, Sun4p) that may participate in DNA replication and/or cell wall septation, according to data for the homologue in *S. cerevisiae*. 45 kDa, 431AAs.

The respective homologous sequence in *K. pastoris* is herein referred to as HCP3 homolog, characterized by an amino acid sequence comprising or consisting of SEQ ID NO:22 (NCBI accession number: BA75_01931 T0 [*Komagataella pastoris*], Gen Bank: ANZ76017.1).

HCP4 (*K. phaffii*): F2QXH5: EPX1, or extracellular protein 1. No clear function has been assigned to this protein, however the respective deletion strain (Δepx1) was produced and found to be more susceptible than the wild type to the cell wall damaging agents Calcofluor white and Congo red, indicating that Epx1 may have a protective role for the cell wall.

The respective homologous sequence in *K. pastoris* is herein referred to as HCP4 homolog, characterized by an amino acid sequence comprising or consisting of SEQ ID NO:23 (NCBI accession number: BA75_00070 T0 [*Komagataella pastoris*]; Gen Bank: ANZ73364.1).

Exemplary further homologous sequences of a HCP described herein which are found in yeast other than *K. phaffii* are as follows:

A homologous sequence of HCP2 in *S. cerevisiae* is herein referred to as HCP2 homolog, characterized by an amino acid sequence comprising or consisting of SEQ ID NO:24 (NCBI accession number: SCW10 [*Saccharomyces cerevisiae*], GenBank: KZVO9161.1; >SCW10 YMR305C SGDID:S000004921).

A further homologous sequence of HCP2 in *S. cerevisiae* is herein referred to as HCP2 homolog, characterized by an amino acid sequence comprising or consisting of SEQ ID NO:25 (NCBI accession number: SCW4 [*Saccharomyces cerevisiae*], GenBank: KZV11513.1; >SCW4 YGR279C SGDID:S000003511).

A homologous sequence of HCP3 in *S. cerevisiae* is herein referred to as HCP3 homolog, characterized by an amino acid sequence comprising or consisting of SEQ ID NO:26 (NCBI accession number: SUN4 [*Saccharomyces cerevisiae*]; GenBank: CAA95939.1; >SUN4 YNL066W SGDID:S000005010).

"Percent (%) amino acid sequence identity" with respect to an amino acid sequence, homologs and orthologues described herein is defined as the percentage of amino acid residues in a candidate sequence that are identical with the amino acid residues in the specific polypeptide sequence, after aligning the sequence and introducing gaps, if necessary, to achieve the maximum percent sequence identity, and not considering any conservative substitutions as part of the sequence identity. Those skilled in the art can determine appropriate parameters for measuring alignment, including any algorithms needed to achieve maximal alignment over the full length of the sequences being compared.

For purposes described herein, the sequence identity between two amino acid sequences is determined using the NCBI BLAST program version 2.2.29 (Jan. 6, 2014) with blastp set at the following exemplary parameters: Program: blastp, Word size: 6, Expect value: 10, Hitlist size: 100, Gapcosts: 11.1, Matrix: BLOSUM62, Filter string: F, Genetic Code: 1, Window Size: 40, Threshold: 21, Composition-based stats: 2.

"Percent (%) identity" with respect to a nucleotide sequence e.g., of a promoter or a gene, is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "isolated" or "isolation" as used herein with respect to a POI shall refer to such compound that has been sufficiently separated from the environment with which it would naturally be associated, in particular a cell culture supernatant, so as to exist in "purified" or "substantially pure" form. Yet, "isolated" does not necessarily mean the exclusion of artificial or synthetic mixtures with other compounds or materials, or the presence of impurities that do not interfere with the fundamental activity, and that may be present, for example, due to incomplete purification. Isolated compounds can be further formulated to produce preparations thereof, and still for practical purposes be isolated—for example, a POI can be mixed with pharmaceutically acceptable carriers or excipients when used in diagnosis or therapy.

The term "purified" as used herein shall refer to a preparation comprising at least 50% (mol/mol), preferably at least 60%, 70%, 80%, 90% or 95% of a compound (e.g., a POI). Purity is measured by methods appropriate for the compound (e.g., chromatographic methods, polyacrylamide gel electrophoresis, HPLC analysis, and the like). An isolated, purified POI as described herein may be obtained by purifying the cell culture supernatants to reduce impurities.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The following standard methods are preferred: cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic interaction chromatography (HIC), Affinity chromatography, size exclusion (SEC) or HPLC Chromatography, POI precipitation of concentration and washing by ultrafiltration steps.

A highly purified product is essentially free from contaminating proteins, in particular from contaminating HCP, and preferably has a purity of at least 90%, more preferred at least 95%, or even at least 98%, up to 100%. The purified products may be obtained by purification of the cell culture supernatant or else from cellular debris.

An isolated and purified POI can be identified by conventional methods such as Western blot, HPLC, activity assay, or ELISA.

The term "recombinant" as used herein shall mean "being prepared by or the result of genetic engineering. A recombinant host may be engineered to delete and/or inactivate one or more nucleotides or nucleotide sequences, and may specifically comprise an expression vector or cloning vector contain a recombinant nucleic acid sequence, in particular employing nucleotide sequence foreign to the host. A recombinant protein is produced by expressing a respective recombinant nucleic acid in a host. The term "recombinant" with respect to a POI as used herein, includes a POI that is prepared, expressed, created or isolated by recombinant means, such as a POI isolated from a host cell transformed to express the POI. In accordance with the present invention conventional molecular biology, microbiology, and recombinant DNA techniques within the skill of the art may be employed. Such techniques are explained fully in the literature. See, e.g., Maniatis, Fritsch & Sambrook, "Molecular Cloning: A Laboratory Manual, Cold Spring Harbor, (1982).

The foregoing description will be more fully understood with reference to the following examples. Such examples are, however, merely representative of methods of practicing one or more embodiments of the present invention and should not be read as limiting the scope of invention.

EXAMPLES

Example 1: Identification of the Host Cell Protein Impurities of *P. pastoris*

To identify the host cell protein (HCP) impurities derived from *P. pastoris* cells (CBS2612 strain) producing a recombinant protein as POI, cell culture supernatant samples were analyzed for HCP composition, content and identity as described below. Three different POIs were expressed in fed-batch cultures using two different expression systems: pG1-3 (SEQ ID NO 38 in WO2017021541), and pAOX1 as e.g., described in Stratton et al., 1998 (High Cell-Density Fermentation. In: Higgins D. R., Cregg J. M. (eds) *Pichia* Protocols. Methods in Molecular Biology, vol 103. Humana Press); including different signal peptides (for POI1: SEQ ID NO 12 of WO2014067926A1, and for POI2 and POI3: the signal peptide of the alpha-mating factor (e.g., SEQ ID NO 1 of U.S. Pat. No. 9,534,039) was used) and each time different fermentations conditions with varying pH and temperature as shown in Table 1 were used. Each sample was tested in triplicate for HCP composition, content and identity.

The reporter proteins are three different proteins: POI1: antigen binding protein of bacterial origin, POI2: artificial antigen binding protein; POI3: antigen binding protein of human origin.

TABLE 1

| Sample | Reporter protein POI | Expression system | pH | Temperature (° C.) | Titer (mg/L) |
| --- | --- | --- | --- | --- | --- |
| 1 | POI 1 | pG1-3 | 5.0 | 30 | 250 |
| 2 | POI 1 | pG1-3 | 6.0 | 30 | 600 |
| 3 | POI 1 | pG1-3 | 6.8 | 30 | 700 |
| 4 | POI 1 | pG1-3 | 6.0 | 25 | 500 |
| 5 | POI 2 | pG1-3 | 4.0 | 25 | 1300 |
| 6 | POI 2 | pG1-3 | 6.0 | 30 | 1500 |
| 7 | POI 3 | pAOX1 | 5.0 | 25 | 3000 |
| 8 | POI 3 | pAOX1 | 5.0 | 25 | 3000 |
| 9 | POI 3 | pG1-3 | 5.0 | 25 | 6000 |
| 10 | POI 3 | pG1-3 | 5.0 | 25 | 4000 |
| 11 | POI 3 | pG1-3 | 5.0 | 25 | 6500 |

Sample Preparation for LC-MS/MS

Samples were denatured in 6.6M guanidine HCl, reduced with TCEP and digested with trypsin prior to analysis: Three replicates were prepared for each sample. 18.5 µl volumes of each sample were transferred into 96-well plate. 90 µl 0.5M MES (2-(N-morpholino)ethanesulfonic acid) pH 5.5, 6.6M guanidine HCl, 10 mM TCEP (Tris(2-carboxyethyl)phosphine) was added to each replicate. Incubation was performed at 50° C. for 30 minutes. All samples were subsequently buffer exchanged using ZebaSpin desalting plate (Thermo) into 0.1M MOPS (3-(N-Morpholino)propanesulfonic acid, 4-Morpholinepropanesulfonic acid) pH 7.3, 2M urea, 2 mM $CaCl_2$, 1 mM TCEP according to the manufacturer's instructions. Digestion was performed with mass spectrometry-grade trypsin (Promega). To 75 µl aliquot of each buffer exchanged sample, 25 µl trypsin digestion solution (4 mg/ml trypsin, 0.1M MOPS pH 7.3, 2M Urea, 2 mM $CaCl_2$), 1 mM TCEP was added and mix. Samples were incubated at 30±2° C. overnight. Digestion was quenched by addition of 2% (final) TFA (trifluoroacetic acid).

LC-MS/MS data Acquisition Data were acquired using a Dionex RSSLnano nanoLC system coupled to a Thermo Fusion Tribrid Q-OT-qIT (Quadrupole-Orbitrap-Linear Ion Trap) mass spectrometer. A 1 µl volume of the tryptic peptides for each sample were injected onto a Acclaim PepMap100 C18, 5 µm, 100 Å, 300 µm i.d.×5 mm Nano-Trap column (Thermo) in a loading buffer of 98:2 water:acetonitrile plus 0.05% TFA at 12 µl/min for 3 minutes. After 3 minutes the nanoLC flow was directed in the reverse direction through the trapping column onto the analytical column (EasySpray PepMap C18 2 µm, 100 Å, 75 µm×25 cm (Thermo)). A linear gradient was applied between 0.1% formic acid in water and 0.08% formic acid in 80:20 acetonitrile:water.

Source ionization settings were static during the acquisition at 2500 V spray voltage and a transfer tube temperature of 275° C. The mass spectrometer was configured in positive ionization mode for acquisition of $MS^1$ data in the orbitrap at 120,000 FWHM nominal resolution with a scan range of 200-2000 m/z, an AGC target of 2.0e5 and a maximum injection time of 50 ms. Data was mass-corrected using an internal standard based on a flouranthine ion lockmass at generated from a separate reagent ion source. Only charge states between z=2 and z=8 were selected for $MS^2$ fragmentation.

$MS^2$ fragmentation was performed in the linear ion trap using a data-dependant decision tree method including HCD and ETD methods. HCD was performed at collision energy of 28%, an AGC target of 1.0e4 and a maximum scan time of 100 ms at the "Normal" trap scan rate. ETD was performed with supplemental activation collision energy of 15%, an AGC target of 1.0e4 and a maximum scan time of 100 ms at the "Normal" trap scan rate.

Mass Spectrometry Data Analysis

Protein identifications based on $MS^2$ fragmentation were performed using PEAKS Studio software. Protein identification was performed for CCCS (clarified cell culture supernatant) only. False discovery rate at the peptide level was controlled at <0.5% using decoy fusion methodology (Zhang, J, et al., "PEAKS DB: de novo sequencing assisted database search for sensitive and accurate peptide identification", Mol. Cell Proteomics 4(11), 111 (2012)). At least 2 unique peptides were required for each protein assignment. Mass tolerances were specified at <5 ppm for parent ions and <0.3 Da for fragment ions.

Generated LC-MSMS data were analyzed separately for each of the three POIs to allow better alignment of the data during processing. Database searching was performed against the proteome for *Komagataella phaffii* (strain ATCC 76273/CBS 7435/CECT 11047/NRRL Y-11430/Wegner 21-1) (Yeast) (*Pichia pastoris*) from UniProt database and using PEAKS studio 7 to identify the proteins present. All samples were processed using Progenesis QI for Proteomics. Identifications from PEAKS were imported into Progenesis for quantitation throughout the experiment. Data for each POI were processed independently. Quantitation was performed using Hi5 methodology. Proteins displaying a significant change in expression profile (q value <0.01) and fold change >2 were evaluated for similarity in expression profile.

Total HCP is determined as follows: For each identified protein, the peak areas of the five most intense peptide signals that derive from that protein are determined and then added together. The resulting number allows comparison of protein abundance on a molar basis (Silva et al., 2006: "Absolute quantification of proteins by LCMSE: a virtue of parallel MS acquisition." Mol Cell Proteomics 5 (1):144-56). The values obtained in this manner for all of the individual HCPs in a test sample were summed together. The resulting summed value is directly proportional to the amount (in mol) of all HCPs in the test sample. Comparison can therefore be made between samples in terms of the percentage or fold-change difference in HCP.

Results

Samples in which the pAOX1 expression system was used showed a significant increase in proteins specific to methanol metabolism (alcohol oxidase, formate dehydrogenase, alcohol dehydrogenase) as well as metabolism of reactive oxygen species which are generated during methanol metabolism (superoxide dismutase, peroxiredoxin PMP, protein disulphide-isomerase, thioredoxin). Additional changes were observed within this experiment, correlating with the high titres for samples 9 and 11 in comparison to samples 7, 8, and 10. These changes included proteins such as ATPases involved in protein folding, GPI-anchored cell surface glycoprotein, Peptidyl-propyl cis transisomerase and uncharacterized protein F2QUJ0 which shows homology to translation elongation factor EF-1 gamma (*Komagataella phaffii*) (C4R6E8). Samples in which the pG1-3 expression system was used displayed an increased expression of enzymes involved in processing carbohydrates (glucanase, glucosidase) as well as structural proteins. Varying fermentation conditions (temperature, pH) was shown to result in changes in the HCP expression profiles, e.g. an increased amount was observed for the chaperone protein HSP90 for fermentation runs at increased temperature and pH.

Surprisingly it was found that only a few different HCPs constitute for the most abundant proteins present in the supernatants of all *Pichia pastoris* cell cultures expressing different POIs under different expression conditions (as described above).

The most abundant HCPs identified are summarized in Table 2 below:

POI3 was expressed under control of the AOX1 promoter in samples 7 and 8, and under control of the G1.3 promoter in samples 9, 10 and 11. While several HCPs specific to one of the two induction systems could be observed, their abundances were negligible compared to the main HCP1, and in lesser extent to the abundances of HCP 2 and 3.

TABLE 2

| HCP | Protein Identifier | Average percentage over all the conditions of the molar amount of the specified HCP to the total molar amount of HCP not taking into account the POI | Amino Acid SEQ ID NO | DNA SEQ ID NO |
|---|---|---|---|---|
| HCP1 | F2QXM5 | 50 | 1 | 2 |
| HCP2 | F2QNG1 | 19 | 3 | 4 |
| HCP3 | F2QQT7 | 6 | 5 | 6 |
| HCP4 | F2QXH5 | 3 | 7 | 8 |

HCP1 and HCP2, together representing between depended on the experiments around 56 and 81% of the total HCP content, on average around 68% of total HCP content. Interestingly, the Epx1 (F2QXH5) protein of Heiss et al. (Appl Microbiol Biotechnol. 2013 February; 97(3):1241-9. doi: 10.1007/s00253-012-4260-4. Epub 2012 Jul. 17) was found to be far less abundant than HCP1, HCP2, or HCP3 alone or in combination, namely accounting for 3% of the total *P. pastoris* HCP.

Example 2: Generation of a HCP1 Knockout Strain in *Pichia*

HCP1 (F2QXM5: identified by SEQ ID NOs:1 and 2) was identified in the host cell protein identification analysis of Example 1, accounting for between 26-64%, on average around 50% of the total HCP load in different *P. pastoris* strains expressing 3 different POIs using different expression systems and fermentation conditions (Example 1):

For the disruption of the gene encoding HCP1 in *P. pastoris* (CBS2612 strain), a split marker cassette approach was used as described by Heiss et al. (Appl Microbiol Biotechnol. 2013; 97(3):1241-9).

Primers used for the disruption of the HCP1 encoding gene are listed in Table 3 below (two overlapping split marker cassettes per knock-out target are used):

TABLE 3

| Primer name | Sequence | SEQ ID NO: |
|---|---|---|
| A_Forward | GAGAGAACTAATGCCCAGATAAACTTGC | 9 |
| A_Reverse | GTTGTCGACCTGCAGCGTACGATCAAGTGAG TGAGTGACTGTTGGTG | 10 |
| B_Forward | CACTCACTTGATCGTACGCTGCAGGTCGACAAC | 11 |
| B_Reverse | CGGTGAGAATGGCAAAAGCTTATG | 12 |
| C_Forward | AAGCCCGATGCGCCAGAGTTG | 13 |
| C_Reverse | GGCTGAGATCTGAGTGGATCTGATATCACCTAA TAAC | 14 |
| D_Forward | TAGGTGATATCAGATCCACTCAGATCTCAGCCA ATCAAGCTG | 15 |
| D_Reverse | CGCTTGGTAATAGACAGTGTTATGTGG | 16 |
| Control Forward | CACAGGTTCATCCACCCCGC | 17 |
| Control Reverse | CCATCTTACAGATTCCAGTCTCTAAGCTGC | 18 |
| Control Forward 2 | CGCCTCGACATCATCTGCCCAGATGC | 27 |
| Control Reverse 2 | CGGGCGACAGTCACATCATGCCCCTG | 28 |
| Control Forward 3 | GGCCAGAATGTAAACAAATGCAGATAAGG | 29 |
| Control Reverse 3 | CGTCACTGCCAGCAGTG | 30 |
| Control Forward 4 | GCTGCCTTCCCTATATCTGATATCAC | 31 |

The primer pairs A_Forward/A_Reverse, B_Forward/B_Reverse, C_Forward/C_Reverse, D_Forward/D_Reverse were used to amplify the fragments A, B, C and D by PCR (Q5 High-Fidelity 2× Master Mix, New England Biolabs). Fragment A for knock-out of HCP1 encoding gene is amplified from genomic *P. pastoris* DNA, starting 1500 bp in 5 prime direction of the respective ATG (of the HCP1 encoding gene) until 1 bp in 5 prime direction of ATG. Fragment D for knock-out of HCP1 encoding gene is amplified from genomic *P. pastoris* DNA, starting 500 bp in 3 prime direction of the respective ATG (of the targeted gene) until 2000 bp in 3 prime direction of ATG. Fragment B consists of the first two thirds of the KanMX selection marker cassette and is amplified from a plasmid comprising the KanMX cassette vector DNA template. Fragment C consists of the last two thirds of the KanMX selection marker cassette and is also amplified from a plasmid comprising the KanMX cassette' vector DNA template. Fragments A and B are annealed together (fragment AB) by overlap PCR using the primers A_Forward and B_Reverse. Fragments C and D are annealed together (fragment CD) by overlap PCR using the primers C_Forward and D_Reverse.

To generate knock-out strains, the four host strains (KO strain 1: CBS2612 strain comprising HCP1 knock out (CBS2612 KO HCP1); KO strain 2: CBS2612 strain comprising a heterologous gene encoding POI1 and comprising HCP1 knock out (CBS2612 KO HCP1+POI1); KO strain 3: CBS2612 strain comprising a heterologous gene encoding POI2 and comprising HCP1 knock out (CBS2612 KO HCP1+POI2); and KO strain 4: CBS2612 strain comprising a heterologous gene encoding POI3 and comprising HCP1 knock out (CBS2612 KO HCP1+POI3)) were transformed with a total of 0.5 μg DNA of fragments AB and CD. Cells were selected on YPD agar plates containing 500 μg/mL Geneticin. Positive knock-outs clones were verified by PCR using the primer pair Control_Forward (binds upstream of fragment A) and Control_Reverse (binds downstream of fragment D). Due to the replacement of a region around the startcodon with the KanMX cassette, PCR product bands of positive knock-out strains are bigger than those of a wild type sequence (FIG. 2). Restriction digests on the PCR products were performed with either EcoRI or NcoI to additionally verify the PCR amplicon. The PCR product of a positive knock-out strain should not be cleaved by EcoRI (4602 bp fragment); while it should be digested by NcoI (1955 bp and 2647 bp fragments) (FIG. 2).

In order to analyze and compare the total host cell protein (HCP) content of a HCP1 knock out strain versus a strain comprising the intact HCP1 locus, strain CBS2612 expressing POI3 (CBS2612 POI3) and a strain comprising in addition also the HCP1 knock out (CBS2612 KO HCP1+POI3), were cultured in fed fed-batch cultivations and the total HCP of the respective culture supernatants was as outlined in Example 1 using the promoter pG1.3 and signal peptide aMF_EAEA (*Saccharomyces cerevisiae* a-mating factor signal peptide with the tetrapeptide EAEA, tetrapeptide EAEA identified as SEQ ID NO:19 for POI3 production. The result of the analysis is shown in Table 4.

TABLE 4

|  | CBS2612 KO HCP1 + POI3 | CBS2612 POI3 |
|---|---|---|
| % concentration; amount of total HCPs | 50% | 100% |

As can be seen from Table 4, a strain comprising a knock out of the HCP1 encoding gene generated around 50% (mol/mol) less total amount of HCPs, as compared to the respective strain comprising the gene encoding HCP1 protein.

Example 3: Generation of Multiple Recombinant Protein Expressing Strains in the *Pichia* HCP1 Knockout Strain To further show the strong reduction in total amount of HCPs upon knocking out HCP1, additional strains were generated. In contrast to Example 2, first the knockout strain was generated, upon which the strain was then transformed with one of three plasmids expressing a protein of interest.

For the disruption of the gene encoding HCP1 in *P. pastoris* (CBS2612 strain) SEQ ID NO:2, the same approach was used as described in Example 2. The HCP1 KO strain was verified by four different PCR reactions (FIG. 3). PCR1 (using primer pair Control Forward and Control Reverse 2, Table 3) is used to verify the 5' side of the integration of the knockout cassette in the correct genomic location and should not give an amplicon in the wild type strain, while an amplicon of 1687 bp should be obtained for the HCP1 KO strain. PCR2 (using primer pair Control Forward 2 and Control Reverse) is used to verify the 3' side of the integration of the knockout cassette in the correct genomic location and should not give an amplicon in the wild type strain, while an amplicon of 1723 bp should be obtained for the HCP1 KO strain. PCR3 (using primer pair Control Forward 3 and Control Reverse) is used to verify the HCP1 genomic location and should give an amplicon of 2172 bp in the wild type strain, while no amplicon should be obtained for the HCP1 KO strain. PCR4 (using primer pair Control Forward 4 and Control Reverse 3) is used to verify that the knocked out fragment of the HCP1 gene has not re-integrated somewhere else in the genome. It should give an amplicon of 115 bp in the wild type strain, while no amplicon should be obtained for the HCP1 KO strain.

In a second step, both the wild type (CBS2612) strain and the HCP1 KO strain were transformed with 1-5 µg of one of three plasmids encoding respectively for POI1, POI2 or POI3 under control of the G1-3 promoter (SEQ ID NO 38 in WO2017021541). Cells were selected on YPD agar plates containing 100-1000 µg/mL Zeocin. Positive clones were analyzed for expression, as described in WO2017021541, with a small adaptation, namely the culture medium was changed to the medium from the Media Development Kit (M-KIT-100, m2pLabs, DE). In addition, the gene copy number (GCN) was analyzed using a method known to persons skilled in the art (e.g Abad et aL, 2010). Eight strains were selected based on similar POI titer and GCN in the wild type and HCP1 KO background.

Example 4: Characterization of the Host Cell Protein Impurities in the Culture Supernatant of the Strains from Example 3

To characterize the HCPs impurities derived from the eight selected strains (Example 3), strains were cultivated in fed-batch fermentations as described in Example 1. End of fermentation samples were used for HCP identification.

The samples were prepared, MS data was acquired and the data was analyzed using workflow similar to the one described in Example 1 with minor changes. The analysis was executed as follows:

Sample Preparation for LC-MS/MS

Samples were denatured in 6.6M guanidine HCl, reduced with TCEP and digested with trypsin prior to analysis: Three replicates were prepared for each sample.60 µl µl volumes of each sample were transferred into 96-well plate. 90 µl 0.5M MES (2-(N-morpholino)ethanesulfonic acid) pH 5.5, 6.6M guanidine HCl, 10 mM TCEP (Tris(2-5 carboxyethyl)phosphine) was added to each replicate. Incubation was performed at 50° C. for 30 minutes. All samples were subsequently buffer exchanged using ZebaSpin desalting plate (Thermo) into 0.1M MOPS (3-(N-Morpholino)propanesulfonic acid, 4-Morpholinepropanesulfonic acid) pH 7.3, 2M urea, 2 mM $CaCl_2$), 1 mM TCEP according to the manufacturer's instructions. Digestion was performed with mass spectrometry-grade trypsin (Promega). To 50 µl aliquot of each buffer exchanged sample, 16.6 µl trypsin digestion solution (4 mg/ml trypsin, 0.1M MOPS pH 7.3, 2M Urea, 2 mM CaCl2, 1 mM TCEP was added and mix. Samples were incubated at 30±2° C. overnight. Digestion was quenched by addition of 2% (final) TFA (trifluoroacetic acid). Samples were dilute 1:10 with digestion buffer.

LC-MS/MS Data Acquisition

Data were acquired using a Dionex RSSLnano nanoLC system coupled to a Thermo Fusion Tribrid Q-OT-qIT (Quadrupole-Orbitrap-Linear Ion Trap) mass spectrometer. A 1 µl volume of the tryptic peptides for each sample were injected onto a Acclaim PepMap100 C18, 5 µm, 100 Å, 300 µm i.d.×5 mm Nano-Trap column (Thermo) in a loading buffer of 98:2 water:acetonitrile plus 0.05% TFA at 12 µl/min for 3 minutes. After 3 minutes the nanoLC flow was directed in the reverse direction through the trapping column onto the analytical column (EasySpray PepMap C18 2 µm, 100 Å, 75 µm×25 cm (Thermo)). A linear gradient was applied between 0.1% formic acid in water and 0.08% formic acid in 80:20 acetonitrile:water. Source ionization settings were static during the acquisition at 2500 V spray voltage and a transfer tube temperature of 275° C. The mass spectrometer was configured in positive ionization mode for acquisition of $MS^1$ data in the orbitrap at 120,000 FWHM nominal resolution with a scan range of 350-1500 m/z, an AGC target of 5.0e5 and a maximum injection time of 150 ms. Data was mass-corrected using an internal standard based on a flouranthine ion lockmass generated from a separate reagent ion source. Only charge states between z=2 and z=8 were selected for $MS^2$ fragmentation. $MS^2$ fragmentation was performed in the linear ion trap using TopN most intense data-dependant mode with HCD methods. HCD was performed at collision energy of 28%, an AGC target of 1.0e4 and a maximum scan time of 100 ms at the "Rapid" trap scan rate.

Mass Spectrometry Data Analysis

Protein identifications based on $MS^2$ fragmentation were performed using PEAKS Studio software. Protein identification was performed for CCCS (clarified cell culture supernatant) only. False discovery rate at the peptide level was controlled at <0.1% using decoy fusion methodology (Zhang, J, et al., "PEAKS DB: de novo sequencing assisted database search for sensitive and accurate peptide identification", Mol. Cell Proteomics 4(11), 111 (2012)). At least 2 unique peptides were required for each protein assignment. Mass tolerances were specified at <5 ppm for parent ions and <0.3 Da for fragment ions. Generated LC-MSMS data were analyzed separately for each of the three POIs to allow better alignment of the data during processing. Database searching was performed against the proteome for *Komagataella phaffii* (strain ATCC 76273/CBS 7435/CECT 11047/NRRL Y-11430/Wegner 21-1) (Yeast) (*Pichia pastoris*) from UniProt database and using PEAKS studio 7 to identify the proteins present. All samples were processed using Progenesis QI for Proteomics. Identifications from PEAKS were imported into Progenesis for quantitation throughout the experiment. Data for each POI were processed independently. Quantitation was performed using Hi3 methodology. Proteins displaying a significant change in expression profile (p value <0.05) and fold change >2 were evaluated for similarity in expression profile. Total HCP is determined as follows: For each identified protein, the peak areas of the three most intense peptide signals that derive from that protein are determined and then added together. The resulting number allows comparison of protein abundance on a molar basis (Silva et al., 2006: "Absolute quantification of proteins by LCMSE: a virtue of parallel MS acquisition." Mol Cell Proteomics 5 (1):144-56). The values obtained in this manner for all of the individual HCPs in a test sample were summed together. The resulting summed value is directly proportional to the amount (in mol) of all HCPs in the test sample. Comparison can therefore be made between samples in terms of the percentage or fold-change difference in HCP.

Results

The surprisingly high abundance of HCP1 in the total HCP pool of non-engineered strains, as seen in Example 1, was confirmed in this experiment (FIG. 4). HCP1 constitutes between 43 and 70% of the total HCP in the supernatant of a wild type strain with or without expression of a recombinant protein.

When comparing the total amount of HCP in wild type strains and HCP1 knockout strains, a reduction in total HCP between 20 and 79% was obtained (FIG. 5). While the wild type strain expressing POI1 had a HCP1 content of over 40% of total HCP, the amount of total HCPs has only dropped by 20%. This is due to the slight upregulation of other HCP in this strain background. Nevertheless, for all strains, knocking out HCP1 has a substantial positive impact on the impurity profile of a recombinant produced protein in the cell free medium, which was unexpected.

The invention claimed is:

1. A method of reducing an amount of total endogenous host cell protein (HCP) in a supernatant of a cell culture of a *Komagataella phaffii* host cell that is engineered to produce a heterologous protein of interest (POI), comprising genetically modifying the host cell to knockout the gene encoding an endogenous host cell protein comprising an amino acid sequence having at least 95% sequence identity to SEQ ID NO:1 (HCP1), wherein said genetic modification reduces the amount of total endogenous host cell proteins in the supernatant of the cell culture by at least 10% (mol/mol) as compared to the cell culture of a comparable host cell without said genetic modification.

2. The method of claim 1, wherein the host cell is further genetically modified to knockout the gene encoding at least one additional endogenous host cell protein which is selected from:
  a) an endogenous host cell protein comprising an amino acid sequence having at least 95% sequence identity to SEQ ID NO:3 (HCP2); or
  b) an endogenous host cell protein comprising an amino acid sequence having at least 95% sequence identity to SEQIDNO: 5 (HCP3).

3. The method of claim 1, wherein the host cell is further genetically modified to knockout the gene encoding an endogenous host cell protein comprising an amino acid sequence having at least 95% sequence identity to SEQ ID NO:7 (HCP4).

4. The method of claim 1, wherein said genetic modification reduces the total amount of endogenous host cell proteins in the supernatant of the cell culture by at least 50% (mol/mol) as compared to the cell culture of a comparable host cell without said genetic modification.

5. The method of claim 1, wherein the host cell comprises an expression cassette comprising one or more regulatory nucleic acid sequences operably linked to a nucleotide sequence encoding the POI, wherein the one or more operably linked nucleic acid sequences are not naturally associated with the nucleotide sequence encoding the POI.

6. The method of claim 1, wherein the POI is a peptide or protein selected from the group consisting of an antigen-binding protein, a therapeutic protein, an enzyme, a peptide, a protein antibiotic, a toxin fusion protein, a carbohydrate-protein conjugate, a structural protein, a regulatory protein, a vaccine antigen, a growth factor, a hormone, a cytokine, a process enzyme, and a metabolic enzyme.

7. A method for producing a protein of interest (POI) in a *Komagataella phaffii* host cell, comprising the steps:
  i) genetically modifying the host cell to knockout the gene encoding an endogenous host cell protein comprising an amino acid sequence having at least 95% sequence identity to SEQ ID NO: 1 (HCP1);
  ii) introducing into the host cell an expression cassette comprising one or more regulatory nucleic acid sequences operably linked to a nucleotide sequence encoding the POI;
  iii) culturing the host cell under conditions to produce the POI; and optionally
  iv) isolating the POI from the cell culture; and optionally
  v) purifying the POI,
  wherein a total amount of endogenous host cell proteins in the supernatant of the cell culture is reduced by at least 10% (mol/mol) as compared to the cell culture of a comparable host cell without said genetic modification.

8. The method of claim 7, wherein the total amount of the endogenous host cell proteins in the genetically modified host cell is reduced by at least 50% (mol/mol) compared to the host cell without the genetic modification.

9. A method of reducing the risk of endogenous host cell protein contaminations of a protein of interest (POI) produced in a host cell culture, comprising culturing a *Komagataella phaffii* host cell that is engineered to produce a heterologous protein of interest (POI), wherein the host cell is engineered by a genetic modification to knockout the gene encoding an endogenous host cell protein comprising an amino acid sequence having at least 95% sequence identity to SEQ ID NO:1 (HCP1), and wherein said genetic modification reduces the total amount of endogenous host cell proteins in the supernatant of the cell culture by at least 10% (mol/mol) as compared to the cell culture of a comparable host cell without said genetic modification, under conditions to produce the POI and isolating the POI from the cell culture.

10. The method of claim 1, wherein said genetic modification reduces the total amount of endogenous host cell proteins in the supernatant of the cell culture by at least 15% (mol/mol) as compared to the cell culture of a comparable host cell without said genetic modification.

11. The method of claim 7, wherein the total amount of endogenous host cell proteins in the supernatant of the cell culture of the genetically modified host cell is reduced by at least 15% (mol/mol) as compared to the cell culture of a comparable host cell without said genetic modification.

12. The method of claim 7, further comprising the step of genetically modifying the host cell to knockout the gene encoding at least one additional endogenous host cell protein which is selected from:

a) an endogenous host cell protein comprising an amino acid sequence having at least 95% sequence identity to SEQ ID NO:3 (HCP2);
b) an endogenous host cell protein comprising an amino acid sequence having at least 95% sequence identity to SEQ ID NO:5 (HCP3);
c) an endogenous host cell protein comprising an amino acid sequence having at least 95% sequence identity to SEQ ID NO:7 (HCP4).

13. The method of claim 1, wherein said endogenous host cell protein comprises the amino acid sequence of SEQ ID NO:1.

14. The method of claim 2, wherein said at least one additional endogenous host cell protein is selected from:
a) an endogenous host cell protein comprising the amino acid sequence of SEQ ID NO:3; or
b) an endogenous host cell protein comprising the amino acid sequence of SEQ ID NO:5.

15. The method of claim 3, wherein the cell is further genetically modified to additionally knockout the gene encoding an endogenous host cell protein comprising the amino acid sequence of SEQ ID NO:7.

* * * * *

SEQUENCE LISTING

<160> NUMBER OF SEQ ID NOS: 31

<210> SEQ ID NO 1
<211> LENGTH: 587
<212> TYPE: PRT
<213> ORGANISM: Komagataella phaffii

<400> SEQUENCE: 1

Met Lys Phe Ala Ile Ser Thr Leu Leu Ile Ile Leu Gln Ala Ala Ala
1               5                   10                  15

Val Phe Ala Ala Phe Pro Ile Ser Asp Ile Thr Val Val Ser Glu Arg
            20                  25                  30

Thr Asp Ala Ser Thr Ala Tyr Leu Ser Asp Trp Phe Val Val Ser Phe
        35                  40                  45

Val Phe Ser Thr Ala Gly Ser Asp Glu Thr Ile Ala Gly Asp Ala Thr
    50                  55                  60

Ile Glu Val Ser Ile Pro Asn Glu Leu Glu Phe Val Gln Tyr Pro Asp
65                  70                  75                  80

Ser Val Asp Pro Ser Val Ser Glu Phe Phe Thr Thr Ala Gly Val Gln
                85                  90                  95

Val Leu Ser Thr Ala Phe Asp Tyr Asp Ser His Val Leu Thr Phe Thr
            100                 105                 110

Phe Ser Asp Pro Gly Gln Val Ile Thr Asp Leu Glu Gly Val Val Phe
        115                 120                 125

Phe Thr Leu Lys Leu Ser Glu Gln Phe Thr Glu Ser Ala Ser Pro Gly
    130                 135                 140

Gln His Thr Phe Asp Phe Glu Thr Ser Asp Gln Thr Tyr Ser Pro Ser
145                 150                 155                 160

Val Asp Leu Val Ala Leu Asp Arg Ser Gln Pro Ile Lys Leu Ser Asn
                165                 170                 175

Ala Val Thr Gly Gly Val Glu Trp Phe Val Asp Ile Pro Gly Ala Phe
            180                 185                 190

Gly Asp Ile Thr Asn Ile Asp Ile Ser Thr Val Gln Thr Pro Gly Thr
        195                 200                 205

Phe Asp Cys Ser Glu Val Lys Tyr Ala Val Gly Ser Ser Leu Asn Glu
    210                 215                 220

Phe Gly Asp Phe Thr Pro Gln Asp Arg Thr Thr Phe Ser Asn Ser
225                 230                 235                 240

Ser Ser Gly Glu Trp Ile Pro Ile Thr Pro Ala Ser Gly Leu Pro Val
                245                 250                 255

Glu Ser Phe Glu Cys Gly Asp Gly Thr Ile Ser Leu Ser Phe Ala Gly
            260                 265                 270

Glu Leu Ala Asp Asp Glu Val Leu Arg Val Ser Phe Leu Ser Asn Leu
        275                 280                 285

Ala Asp Asp Val Leu Glu Val Gln Asn Val Val Asn Val Asp Leu Thr
    290                 295                 300

Thr Ala Asp Ser Arg Lys Arg Ala Leu Thr Ser Phe Val Leu Asp Glu
305                 310                 315                 320

Pro Phe Tyr Arg Ala Ser Arg Thr Asp Thr Ala Ala Phe Glu Ala Phe
                325                 330                 335

Ala Ala Val Pro Ala Asp Gly Asp Ile Thr Ser Thr Ser Thr Ala Ile
            340                 345                 350

Thr Ser Val Thr Ala Thr Val Thr His Thr Val Thr Ser Val Cys
        355                 360                 365

Tyr Val Cys Ala Glu Thr Pro Val Thr Val Thr Tyr Thr Ala Pro Val
370                 375                 380

Ile Thr Asn Pro Ile Tyr Tyr Thr Thr Lys Val His Val Cys Asn Val
385                 390                 395                 400

Cys Ala Glu Thr Pro Ile Thr Tyr Thr Val Thr Ile Pro Cys Glu Thr
            405                 410                 415

Asp Glu Tyr Ala Pro Ala Lys Pro Thr Gly Thr Glu Gly Glu Lys Ile
            420                 425                 430

Val Thr Val Ile Thr Lys Glu Gly Gly Asp Lys Tyr Thr Lys Thr Tyr
            435                 440                 445

Glu Glu Val Thr Tyr Thr Lys Thr Tyr Pro Lys Gly Gly His Glu Asp
450                 455                 460

His Ile Val Thr Val Lys Thr Lys Glu Gly Gly Glu Lys Val Thr Lys
465                 470                 475                 480

Thr Tyr Glu Glu Val Thr Tyr Thr Lys Gly Pro Glu Ile Val Thr Val
                485                 490                 495

Val Thr Lys Glu Gly Gly Glu Lys Val Thr Thr Thr Tyr His Asp Val
            500                 505                 510

Pro Glu Val Val Thr Val Ile Thr Lys Glu Gly Gly Glu Lys Val Thr
            515                 520                 525

Thr Thr Tyr Pro Ala Thr Tyr Pro Ala Thr Tyr Thr Glu Gly His Ser
530                 535                 540

Ala Gly Val Pro Thr Ser Ala Ser Thr Pro Pro Gln Ala Thr Tyr Thr
545                 550                 555                 560

Val Ser Glu Ala Gln Val Asn Leu Gly Ser Lys Ser Ala Val Gly Leu
            565                 570                 575

Leu Ala Ile Val Pro Met Leu Phe Leu Ala Ile
            580                 585

<210> SEQ ID NO 2
<211> LENGTH: 1764
<212> TYPE: DNA
<213> ORGANISM: Komagataella phaffii

<400> SEQUENCE: 2
atgaagttcg caatttcaac acttcttatt atcctacagg ctgccgctgt ttttgctgcc    60
ttccctatat ctgatatcac agttgtcagt gaaagaactg acgcatcgac tgcctatctg   120
tcggactggt tgttgtttc attcgttttt agcactgctg gcagtgacga acaatcgct    180 ggtgacgcta ctattgaagt ctctattcct aatgagctag agtttgttca ataccctgat   240
tccgttgacc catccgtttc cgaattcttt acaaccgctg gtgttcaagt tttgagtacc   300
gcatttgatt atgacagcca tgttttgact ttcactttct ctgacccagg tcaagttatt   360
actgaccttg aaggagttgt tttctttaca ctcaaactca gtgagcagtt caccgagtct   420 gcttccctg ccaacacac cttcgacttc gaaacctctg atcagaccta cagtccttct    480
gtcgacttgg tcgcacttga cagatctcag ccaatcaagc tgagcaacgc tgtgaccggt   540
ggtgttgaat ggtttgttga tattccaggt gcatttggag acatcaccaa cattgacatc   600
agcactgttc agaccccagg taccttgac tgttcggagg ttaagtatgc tgtcggaagc    660
agcctgaacg aatttggtga ctttaccccca caggatagaa caactttctt cagcaattcg   720
tccagtggag aatggattcc aattactcct gcttcaggtc ttccagttga aagctttgag   780
tgtggtgatg gtaccatctc tttgagcttt gccggtgaat tagctgacga tgaagttctt   840
agagtttctt tcctatcaaa cctggctgat gatgttcttg aagttcagaa cgttgtgaat   900

```
gttgacctca ccactgcaga ctcgcgtaag agagcattga cttcgttcgt ccttgatgag      960
ccatttacc gtgctagcag aaccgacaca gctgccttcg aagcttttgc agccgtacca     1020
gctgacggag atattacttc tacttcaact gccattacca gtgttactgc aacagttacc     1080
cacaccactg ttcatccgt ctgttacgtt tgtgctgaaa ctcctgttac cgttacctac      1140
accgctccag tcattactaa cccaatttac tataccacta aggttcacgt ttgtaacgtc     1200
tgtgctgaaa caccaattac ctacactgtt accattcctt gtgaaactga tgaatacgct     1260
ccagctaagc caactggcac tgagggtgag aagatcgtca ccgttattac aaaagaaggt     1320
ggtgacaagt acaccaagac atacgaagaa gtcacttaca ccaagactta tcccaagggt     1380
ggtcatgagg accatattgt cactgtcaaa actaaagaag gtggtgaaaa ggtcactaag     1440
acttacgagg aagtcaccta taccaagggt cctgaaattg ttactgttgt taccaaggag     1500
ggtggggaga aagttaccac tacttaccac gatgttcctg aggttgttac tgttatcacc     1560
aaggaaggtg agagaaagt tactactact acccagcta cttacccagc tacctacaca       1620
gaaggccaca gtgctggagt tccaacaagt gctagcaccc ctcctcaagc tacttacact     1680
gtgagtgagg ctcaagtcaa cttgggttcc aaatctgctg ttggtctgtt agcaatcgtc     1740
ccaatgctct tcttggctat ctaa                                            1764
```

<210> SEQ ID NO 3
<211> LENGTH: 348
<212> TYPE: PRT
<213> ORGANISM: Komagataella phaffii

<400> SEQUENCE: 3

```
Met Gln Val Lys Ser Ile Val Asn Leu Leu Leu Ala Cys Ser Leu Ala
1               5                   10                  15

Val Ala Arg Pro Leu Glu His Ala His His Gln His Asp Lys Arg Gly
                20                  25                  30

Val Val Val Val Thr Lys Thr Ile Val Val Asp Gly Ser Thr Val Glu
            35                  40                  45

Ala Thr Ala Ala Ala Gln Val Gln Glu His Ala Glu Thr Phe Ala Glu
        50                  55                  60

Ser Thr Pro Ser Ala Val Val Ser Ser Ser Ala Pro Ser Ala
65                  70                  75                  80

Ser Ser Ala Ser Ala Pro Ala Ser Ser Gly Ser Phe Ser Ala Gly Thr
                85                  90                  95

Lys Gly Val Thr Tyr Ser Pro Tyr Gln Ala Gly Gly Cys Lys Thr
            100                 105                 110

Ala Glu Glu Val Ala Ser Asp Leu Ser Gln Leu Thr Gly Tyr Glu Ile
        115                 120                 125

Ile Arg Leu Tyr Gly Val Asp Cys Asn Gln Val Glu Asn Val Phe Lys
    130                 135                 140

Ala Lys Ala Pro Gly Gln Lys Leu Phe Leu Gly Ile Phe Phe Val Asp
145                 150                 155                 160

Ala Ile Glu Ser Gly Val Ser Ala Ile Ala Ser Ala Val Lys Ser Tyr
                165                 170                 175

Gly Ser Trp Asp Asp Val His Thr Ser Val Gly Asn Glu Leu Val
            180                 185                 190

Asn Asn Gly Glu Ala Thr Val Ser Gln Ile Gly Gln Tyr Val Ser Thr
        195                 200                 205

Ala Lys Ser Ala Leu Arg Ser Ala Gly Phe Thr Gly Pro Val Leu Ser
```

Val Asp Thr Phe Ile Ala Val Ile Asn Asn Pro Gly Leu Cys Asp Phe
225                 230                 235                 240

Ala Asp Glu Tyr Val Ala Val Asn Ala His Ala Phe Phe Asp Gly Gly
            245                 250                 255

Ile Ala Ala Ser Gly Ala Gly Asp Trp Ala Ala Glu Gln Ile Gln Arg
        260                 265                 270

Val Ser Ser Ala Cys Gly Gly Lys Asp Val Leu Ile Val Glu Ser Gly
    275                 280                 285

Trp Pro Ser Lys Gly Asp Thr Asn Gly Ala Ala Val Pro Ser Lys Ser
290                 295                 300

Asn Gln Gln Ala Ala Val Gln Ser Leu Gly Gln Lys Ile Gly Ser Ser
305                 310                 315                 320

Cys Ile Ala Phe Asn Ala Phe Asn Asp Tyr Trp Lys Ala Asp Gly Pro
            325                 330                 335

Phe Asn Ala Glu Lys Tyr Trp Gly Ile Leu Asp Ser
        340                 345

<210> SEQ ID NO 4
<211> LENGTH: 1047
<212> TYPE: DNA
<213> ORGANISM: Komagataella phaffii

<400> SEQUENCE: 4
atgcaagtta aatctatcgt taacctactg ttggcatgtt cgttggccgt ggccagacct      60
ttggagcacg cccaccatca acatgacaag agaggtgttg tcgtcgtgac caagaccatc     120
gttgtcgatg gttccaccgt tgaggctacc gcagcagccc aggtccaaga gcacgctgaa     180
actttcgcag agtcgactcc ttcagctgtt gtttccagtt catcagctcc ttcctctgct     240
tcttctgctt ccgctcctgc ctcttccggt agcttctccg ctggaaccaa aggtgtcacc     300
tactctcctt accaagccgg tggtggctgt aagactgcag aggaggtcgc ttccgatctt     360
tcccagttga ccggctacga gatcatcaga ttgtacggtg ttgactgtaa ccaagtcgag     420
aacgtcttca aggccaaggc cccaggtcaa aagttgtttt tgggaatctt ctttgttgat     480
gctatcgaga gcggtgtcag tgctattgcc tccgctgtca agtcatacgg ttcttgggac     540
gatgtccaca ctgtctctgt tggtaacgag ttggtcaaca acggtgaggc cactgtttcc     600
caaatcggtc aatacgtttc taccgctaaa tctgccttga gatctgctgg tttcaccggt     660
ccagttcttt ctgtcgacac tttcattgct gtcatcaaca cccagggtt gtgtgacttt     720
gctgacgagt acgttgccgt taacgctcac gctttctttg acggtggcat tgctgcctct     780
ggagctggtg attgggctgc tgagcagatc caaagagttt cttccgcttg tggtggcaag     840
gatgtcctca ttgtcgagtc cggatggcct tcaaagggag acaccaacgg tgctgccgtt     900
ccttccaagt caaaccaaca ggctgctgtc caatctctag gtcagaagat cggttcttct     960
tgtattgctt tcaacgcttt caacgattac tggaaggccg atggtccttt caacgctgag    1020
aagtactggg gtatcctaga ctcctaa                                        1047

<210> SEQ ID NO 5
<211> LENGTH: 431
<212> TYPE: PRT
<213> ORGANISM: Komagataella phaffii

<400> SEQUENCE: 5

Met Lys Ile Ser Ala Leu Thr Ala Cys Ala Val Thr Leu Ala Gly Leu

```
1               5                   10                  15
Ala Ile Ala Ala Pro Ala Pro Lys Pro Glu Asp Cys Thr Thr Thr Val
                20                  25                  30
Gln Lys Arg His Gln His Lys Arg Ala Val Ala Tyr Asp Tyr Val Tyr
            35                  40                  45
Val Thr Val Thr Ile Asn Gly Gln Gly Glu Thr Ile Ser Pro Thr Val
        50                  55                  60
Val Ala Glu Leu Glu Thr Val Ser Thr Pro Ala Thr Ser Ser Ser Ala
65                  70                  75                  80
Val Ala Thr Ser Ser Ala Pro Ala Thr Ser Ser Ile Pro Glu Thr
                85                  90                  95
Thr Ser Ala Gln Val Thr Thr Ser Ser Val Ala Glu Ser Thr Ser Ala
                100                 105                 110
Gln Phe Thr Ser Ser Thr Glu Glu Ala Ser Ser Ser Val Glu Gln Thr
            115                 120                 125
Thr Gln Ser Ser Ser Ser Ser Pro Ser Ser Ser Ser Ser Ser Ser
        130                 135                 140
Ser Ser Ser Gly Ser Ser Ser Gly Ser Ser Ser Gly Gly Ile Asp Gly
145                 150                 155                 160
Asp Leu Ser Trp Tyr Ser Gly Pro Gly Asn Lys Phe Gln Asp Gly Thr
                165                 170                 175
Ile Lys Cys Ser Glu Phe Pro Ser Gly Asn Gly Val Val Ala Leu Asp
            180                 185                 190
His Leu Gly Phe Gly Gly Trp Ser Gly Leu Tyr His Pro Ser Asp Thr
            195                 200                 205
Ser Thr Gly Gly Ile Cys Glu Pro Asp Thr Tyr Cys Ser Tyr Ala Cys
    210                 215                 220
Gln Ser Gly Met Ser Lys Thr Gln Trp Pro Ser Glu Gln Pro Asp Asn
225                 230                 235                 240
Gly Val Ser Val Gly Gly Leu Tyr Cys Asp Ser Asp Gly Tyr Leu Tyr
                245                 250                 255
Arg Ser Lys Lys Asp Thr Asp Tyr Leu Cys Glu Trp Gly Ile Asp Val
                260                 265                 270
Ala Tyr Val Val Ser Glu Ile Gly Lys Thr Ala Ala Ile Cys Arg Thr
            275                 280                 285
Asp Tyr Pro Gly Thr Glu Asn Met Val Ile Pro Thr Val Val Ser Pro
            290                 295                 300
Gly Gly Glu Leu Pro Leu Thr Thr Val Asp Gln Ser Ser Tyr Tyr Thr
305                 310                 315                 320
Trp Arg Gly Met Lys Thr Ser Ala Gln Tyr Tyr Val Asn Asp Ala Gly
                325                 330                 335
Val Asp Trp Thr Thr Gly Cys Thr Trp Gly Asp Tyr Gly Thr Asp Tyr
            340                 345                 350
Gly Asn Trp Ala Pro Leu Asn Phe Gly Ala Gly Tyr Asp Asn Gly Ile
            355                 360                 365
Ser Tyr Leu Ser Leu Ile Pro Asn Pro Asn Asn Lys Asp Ser Leu Asn
        370                 375                 380
Tyr Asn Val Lys Ile Val Ala Tyr Asp Asp Ser Ser Val Ile Gly
385                 390                 395                 400
Glu Cys Lys Tyr Glu Asn Gly Ser Tyr Asn Gly Asn Gly Ser Asp Gly
                405                 410                 415
Cys Thr Val Ala Val Asn Ser Gly Lys Ala Lys Phe Val Leu Tyr
            420                 425                 430
```

<210> SEQ ID NO 6
<211> LENGTH: 1296
<212> TYPE: DNA
<213> ORGANISM: Komagataella phaffii

<400> SEQUENCE: 6

```
atgaagatat ccgctcttac agcctgcgct gttactctag ctggtcttgc aattgcagca      60
ccagctccaa agcctgaaga ttgtactact acagtgcaga acgtcacca acacaaacgt     120
gctgtcgcat acgattacgt ttatgtcaca gtgactatca atggccaagg tgaaaccatt     180
tctccaactg ttgtggcaga acttgagacg gtttccacgc ctgcaacaag ctcatccgca     240
gttgcaactt cttctgctcc tgcaaccact tcttcaatcc agagacaac ttctgcacaa     300
gtgaccacct cttctgttgc agagtccact tcagcgcaat tcacttcatc taccgaagaa     360
gcctcttctt ctgttgagca aacgactcaa tcaagttcaa gttcaagtcc aagttccagt     420
tccagttcaa gttcgagctc aggctctagt tcaggatcca gttccggtgg aatcgatgga     480
gacctaagct ggtactcagg tcctggaaac aaattccagg atggtactat aaagtgttcc     540
gagttcccat ccggtaacgg tgttgttgcc ttggaccatc tcggattcgg aggatggtca     600
ggattatacc acccatctga tacctctact ggtgggatct gtgaaccaga cacctactgc     660
tcttatgcct gccaatcagg tatgtcgaag acacaatggc catctgaaca accggacaat     720
ggtgttttccg ttggtggtct gtattgtgat tctgatggat accttaccg ttccaagaaa     780
gacactgact atctatgtga atggggtatt gatgtcgcct atgttgtcag tgaaattggt     840
aaaactgctg ccatctgtag aaccgactat ccaggaactg aaaacatggt tataccaact     900
gttgtgagtc cgggtggaga actccctctg acaacagttg accaatcctc ttactatacg     960
tggagggaa tgaagacttc ggcccaatac tacgtgaacg atgctggtgt tgactggacc    1020
accggttgta cctggggaga ctatggaacc gactacggta actgggcgcc attgaacttt    1080
ggtgccggtt acgacaacgg catttcatac ctttctttaa tccctaaccc taacaacaag    1140
gactccttga actataatgt caagattgtt gcttatgatg attcttctgt cgttatcggc    1200
gagtgcaagt atgaaaatgg ttcatacaat ggaaacggtt ccgacggttg taccgttgct    1260
gtcaacagcg gtaaggccaa gtttgtgttg tattaa                             1296
```

<210> SEQ ID NO 7
<211> LENGTH: 313
<212> TYPE: PRT
<213> ORGANISM: Komagataella phaffii

<400> SEQUENCE: 7

Met Lys Leu Ser Thr Asn Leu Ile Leu Ala Ile Ala Ala Ala Ser Ala
1               5                   10                  15

Val Val Ser Ala Ala Pro Val Ala Pro Ala Glu Glu Ala Ala Asn His
            20                  25                  30

Leu His Lys Arg Ala Tyr Tyr Thr Asp Thr Thr Lys Thr His Thr Phe
        35                  40                  45

Thr Glu Val Val Thr Val Tyr Arg Thr Leu Lys Pro Gly Glu Ser Ile
    50                  55                  60

Pro Thr Asp Ser Pro Ser His Gly Gly Lys Ser Thr Lys Lys Gly Lys
65                  70                  75                  80

Gly Ser Thr Thr His Ser Gly Ala Pro Gly Ala Thr Ser Gly Ala Pro
                85                  90                  95

Thr Asp Asp Thr Thr Ser Thr Ser Gly Ser Val Gly Leu Pro Thr Ser
            100                 105                 110

Ala Thr Ser Val Thr Ser Ser Thr Ser Ser Ala Ser Thr Thr Ser Ser
        115                 120                 125

Gly Thr Ser Ala Thr Ser Thr Gly Thr Gly Thr Ser Thr Ser Thr Ser
    130                 135                 140

Thr Gly Thr Gly Thr Gly Thr Thr Gly Thr Gly Thr Thr Ser Ser Ser
145                 150                 155                 160

Thr Ser Ser Ser Ala Thr Ser Thr Pro Thr Gly Ser Ile Asp Ala Ile
                165                 170                 175

Ser Gln Thr Leu Leu Asp Thr His Asn Asp Lys Arg Ala Leu His Gly
            180                 185                 190

Val Pro Asp Leu Thr Trp Ser Thr Glu Leu Ala Asp Tyr Ala Gln Gly
        195                 200                 205

Tyr Ala Asp Ser Tyr Thr Cys Gly Ser Ser Leu Glu His Thr Gly Gly
    210                 215                 220

Pro Tyr Gly Glu Asn Leu Ala Ser Gly Tyr Ser Pro Ala Gly Ser Val
225                 230                 235                 240

Glu Ala Trp Tyr Asn Glu Ile Ser Asp Tyr Asp Phe Ser Asn Pro Gly
                245                 250                 255

Tyr Ser Ala Gly Thr Gly His Phe Thr Gln Val Val Trp Lys Ser Thr
            260                 265                 270

Thr Gln Leu Gly Cys Gly Tyr Lys Glu Cys Ser Thr Asp Arg Tyr Tyr
        275                 280                 285

Ile Ile Cys Glu Tyr Ala Pro Arg Gly Asn Ile Val Ser Ala Gly Tyr
    290                 295                 300

Phe Glu Asp Asn Val Leu Pro Pro Val
305                 310

<210> SEQ ID NO 8
<211> LENGTH: 939
<212> TYPE: DNA
<213> ORGANISM: Komagataella phaffii

<400> SEQUENCE: 8
atgaagctct ccaccaattt gattctagct attgcagcag cttccgccgt tgtctcagct     60
gctccagttg ctccagccga agaggcagca aaccacttgc acaagcgtgc ttactacacc    120
gacacaacca agactcacac tttcactgag gttgttactg tctaccgaac tttgaaaccg    180
ggcgaaagta tcccaactga ctctccaagc cacggtggta aaagtactaa aaagggtaag    240
ggtagtacca ctcactctgg tgctccagga gctacctctg tgctccaac tgacgacacc    300 acttcgacta gtggctcagt agggttacca actagcgcaa cttcagttac tcttctacc     360 tcctctgcaa gtacaacaag cagtggaact tcagccacta gcactggtac cggtactagc    420
actagcacta gcactggtac tggtactggt actacaggca caggaaccac tagttccagc    480
actagctctt ctgctacttc gactccaacc ggttctatcg acgctatcag ccagacactt    540
ctggatactc acaatgataa gcgtgctttg cacggcgtcc cagaccttac ttggtctacc    600
gaactcgctg actacgccca aggttacgcc gattcataca cttgtggctc ttcattagaa    660
cacacaggtg gaccatacgg tgaaaatttg gcctctggat actctcctgc tggcagtgta    720
gaagcatggt acaacgagat cagcgactac gatttctcta acccaggtta ttctgctggt    780
accggtcact tcacccaagt tgtctggaaa tcaactacac agctgggctg tggatacaag    840
gagtgcagta ccgacagata ctacatcatc tgcgaatacg cacctcgtgg aaatattgtt    900
tctgccggct acttcgaaga caacgtcctg cctcctgtt                        939

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
gagagaacta atgcccagat aaacttgc                                    28

<210> SEQ ID NO 10
<211> LENGTH: 47
<212> TYPE: DNA
<213> ORGANISM: Artificial Sequence
<220> FEATURE:
<223> OTHER INFORMATION: Primer

<400> SEQUENCE: 10
gttgtcgacc tgcagcgtac gatcaagtga gtgagtgact gttggtg               47

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
cactcacttg atcgtacgct gcaggtcgac aac                              33

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
cggtgagaat ggcaaaagct tatg                                        24

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
aagcccgatg cgccagagtt g                                           21

<210> SEQ ID NO 14
<211> LENGTH: 37
<212> TYPE: DNA
<213> ORGANISM: Artificial Sequence
<220> FEATURE:
<223> OTHER INFORMATION: Primer

<400> SEQUENCE: 14
ggctgagatc tgagtggatc tgatatcacc taataac                          37

<210> SEQ ID NO 15
<211> LENGTH: 42
<212> TYPE: DNA

-continued

<210> SEQ ID NO 15
<211> LENGTH: 42
<212> TYPE: DNA
<213> ORGANISM: Artificial Sequence
<220> FEATURE:
<223> OTHER INFORMATION: Primer

<400> SEQUENCE: 15
taggtgatat cagatccact cagatctcag ccaatcaagc tg        42

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
cgcttggtaa tagacagtgt tatgtgg        27

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
cacaggttca tccaccccgc        20

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
ccatcttaca gattccagtc tctaagctgc        30

<210> SEQ ID NO 19
<211> LENGTH: 4
<212> TYPE: PRT
<213> ORGANISM: Artificial Sequence
<220> FEATURE:
<223> OTHER INFORMATION: Tetrapeptide

<400> SEQUENCE: 19

Glu Ala Glu Ala
1

<210> SEQ ID NO 20
<211> LENGTH: 615
<212> TYPE: PRT
<213> ORGANISM: Komagataella pastoris

<400> SEQUENCE: 20

Met Gln Leu Arg Val Ser Phe Ser Phe Asp Tyr Lys Asn Gly Gly Tyr
1               5                   10                  15

Pro Trp Thr Tyr Phe Asp Phe Pro His Thr Val Thr His Leu Ile Met
            20                  25                  30

Lys Phe Ala Ile Pro Thr Leu Phe Val Ile Leu Gln Ala Ala Ser Val
        35                  40                  45

Phe Ala Ala Phe Pro Ile Thr Asp Ile Thr Val Val Ser Glu Arg Thr
    50                  55                  60

Asp Ala Ser Ile Ala Tyr Leu Ser Asp Trp Phe Leu Val Ser Phe Val
65                  70                  75                  80

```
Phe Ser Thr Ala Gly Ser Asp Glu Thr Leu Ala Gly Asp Ala Thr Ile
                85                  90                  95

Glu Val Ser Ile Pro Asp Glu Leu Glu Phe Val Gln Tyr Pro Glu Ser
                100                 105                 110

Val Asp Pro Ser Val Ser Glu Phe Phe Thr Thr Ala Gly Val Gln Val
                115                 120                 125

Leu Ser Thr Ala Phe Asp Tyr Asp Ser His Val Leu Thr Phe Thr Phe
130                 135                 140

Ser Asp Pro Gly Gln Val Ile Thr Glu Leu Glu Gly Val Val Tyr Phe
145                 150                 155                 160

Thr Leu Lys Leu Ser Glu Gln Phe Thr Glu Ser Ala Thr Pro Gly Gln
                165                 170                 175

His Thr Phe Asp Phe Glu Thr Ser Asp Gln Val Tyr Ser Pro Ser Val
                180                 185                 190

Asp Leu Val Ala Leu Asp Arg Thr Gln Pro Ile Lys Leu Ser Asn Ala
                195                 200                 205

Val Thr Gly Gly Val Glu Trp Phe Val Asp Ile Pro Gly Ala Phe Gly
                210                 215                 220

Asp Ile Thr Asn Ile Asp Ile Ser Thr Val Gln Thr Pro Gly Thr Phe
225                 230                 235                 240

Asp Cys Ser Glu Val Lys Tyr Ala Val Gly Ser Ser Leu Asn Glu Phe
                245                 250                 255

Gly Asp Phe Thr Pro Gln Asp Arg Thr Thr Phe Phe Ser Asn Ser Ser
                260                 265                 270

Ser Gly Glu Trp Ile Pro Ile Thr Pro Ala Ser Gly Leu Pro Val Glu
                275                 280                 285

Ser Phe Glu Cys Gly Asp Gly Thr Ile Ser Leu Ser Phe Ala Gly Glu
                290                 295                 300

Leu Ala Asp Asp Glu Val Leu Arg Val Ser Phe Leu Ser Asn Leu Asp
305                 310                 315                 320

Asp Asp Val Leu Glu Val Gln Asn Val Asn Val Asp Leu Thr Thr
                325                 330                 335

Ala Asp Ser Arg Lys Arg Ala Leu Thr Ser Phe Val Leu Asp Glu Pro
                340                 345                 350

Phe Tyr Arg Ala Ser Arg Thr Asp Pro Ala Ala Phe Glu Ala Phe Ala
                355                 360                 365

Ala Val Pro Ala Asp Gly Asp Ile Thr Thr Thr Ser Thr Ala Thr Thr
                370                 375                 380

Ser Val Thr Ala Thr Val Thr Glu Thr Thr Val Thr Ser Val Cys Tyr
385                 390                 395                 400

Val Cys Ala Glu Thr Pro Val Thr Val Thr Tyr Thr Ala Pro Val Ile
                405                 410                 415

Thr Asn Pro Ile Tyr Tyr Thr Thr Lys Val His Val Cys Asn Val Cys
                420                 425                 430

Ala Glu Thr Pro Ile Thr Tyr Thr Val Thr Ile Pro Cys Glu Ser Asp
                435                 440                 445

Glu Tyr Ala Pro Ala Lys Pro Thr Gly Thr Lys Gly Glu Lys Ile Val
450                 455                 460

Thr Val Val Thr Lys Glu Gly Asp Lys Tyr Thr Lys Thr Tyr Glu
465                 470                 475                 480

Glu Val Thr Tyr Thr Lys Thr Tyr Pro Lys Glu Gly Gly His Glu Asp
                485                 490                 495
```

```
His Ile Val Thr Val Thr Thr Lys Glu Gly Gly Glu Lys Val Thr Lys
            500                 505                 510

Thr Tyr Glu Glu Val Thr Tyr Thr Lys Gly Pro Glu Ile Val Thr Val
        515                 520                 525

Val Thr Lys Glu Gly Gly Glu Glu Val Thr Lys Thr Tyr His Asp Val
    530                 535                 540

Pro Glu Val Val Thr Val Thr Lys Glu Gly Gly Glu Lys Val Thr
545                 550                 555                 560

Thr Thr Tyr Pro Ala Thr Tyr Thr Glu Gly Pro Gly Ala Val Pro Thr
                565                 570                 575

Ser Val Ser Ala Pro Pro Lys Ala Thr Tyr Thr Val Ser Glu Ala Asp
            580                 585                 590

Val Asn Leu Gly Ser Arg Ser Ala Ala Val Gly Leu Leu Ala Ile Leu
        595                 600                 605

Pro Met Leu Phe Leu Ala Val
        610                 615

<210> SEQ ID NO 21
<211> LENGTH: 348
<212> TYPE: PRT
<213> ORGANISM: Komagataella pastoris

<400> SEQUENCE: 21

Met Gln Val Lys Ser Ile Val Asn Leu Leu Ala Cys Ser Leu Ala
1               5                   10                  15

Val Ala Arg Pro Leu Glu His Ala His His Gln His Asp Lys Arg Gly
            20                  25                  30

Val Val Val Thr Lys Thr Ile Ile Val Asp Gly Ser Thr Val Glu
        35                  40                  45

Ala Thr Ala Ala Ala Gln Val Gln Glu His Ala Glu Thr Ile Ala Glu
    50                  55                  60

Ser Thr Pro Ser Ala Val Val Ala Ser Ala Ala Pro Ser Ala Ala
65                  70                  75                  80

Ser Ser Ala Ser Ala Pro Ala Ser Ser Gly Ser Phe Ser Ala Gly Thr
            85                  90                  95

Lys Gly Val Thr Tyr Ser Pro Tyr Gln Ala Gly Gly Cys Lys Thr
        100                 105                 110

Ala Glu Glu Val Ala Ser Asp Leu Ser Gln Leu Thr Asp Tyr Glu Ile
    115                 120                 125

Ile Arg Leu Tyr Gly Val Asp Cys Asn Gln Val Glu Asn Val Phe Lys
130                 135                 140

Ala Lys Ala Pro Gly Gln Lys Leu Phe Leu Gly Ile Phe Phe Val Asp
145                 150                 155                 160

Ala Ile Glu Ser Gly Val Ser Ala Ile Ala Ser Ala Val Ser Ser Tyr
            165                 170                 175

Gly Ser Trp Asn Asp Val His Thr Val Ser Val Gly Asn Glu Leu Val
        180                 185                 190

Asn Asn Gly Glu Ala Thr Val Ser Gln Ile Gly Gln Tyr Val Ser Thr
    195                 200                 205

Ala Lys Ser Ala Leu Arg Ser Ala Gly Phe Thr Gly Pro Val Leu Ser
    210                 215                 220

Val Asp Thr Phe Ile Ala Val Ile Asn Asn Pro Gly Leu Cys Asp Phe
225                 230                 235                 240

Ala Asp Glu Tyr Val Ala Val Asn Ala His Ala Phe Phe Asp Gly His
            245                 250                 255
```

```
Ile Ala Ala Ser Gly Ala Gly Asp Trp Ala Glu Gln Ile Gln Arg
            260                 265                 270

Val Ser Ser Ala Cys Gly Gly Lys Asp Val Leu Ile Val Glu Ser Gly
            275                 280                 285

Trp Pro Ser Lys Gly Asp Thr Asn Gly Ala Ala Val Pro Ser Lys Ser
290                 295                 300

Asn Gln Gln Ala Ala Val Gln Ser Leu Gly Gln Lys Ile Gly Ser Ser
305                 310                 315                 320

Cys Ile Ala Phe Asn Ala Phe Asn Asp Tyr Trp Lys Ala Asp Gly Pro
                325                 330                 335

Phe Asn Ala Glu Lys Tyr Trp Gly Ile Leu Asp Ser
            340                 345

<210> SEQ ID NO 22
<211> LENGTH: 430
<212> TYPE: PRT
<213> ORGANISM: Komagataella pastoris

<400> SEQUENCE: 22

Met Lys Ile Ser Ala Leu Thr Ala Cys Ala Val Thr Leu Ala Gly Leu
1               5                   10                  15

Ala Ile Ala Ala Pro Ala Pro Lys Pro Glu Asp Cys Thr Thr Thr Val
                20                  25                  30

Gln Lys Arg His Gln His Lys Arg Ala Val Ala Tyr Asp Tyr Val Tyr
            35                  40                  45

Val Thr Val Thr Ile Asn Gly Gln Gly Glu Thr Ile Ser Pro Thr Val
50                  55                  60

Val Ala Glu Leu Glu Thr Ala Ser Thr Pro Ala Thr Ser Ser Ser Ala
65                  70                  75                  80

His Val Glu Thr Ser Ser Ala Pro Ala Thr Thr Ser Ser Val Pro Glu
                85                  90                  95

Thr Thr Ser Ala Glu Gln Thr Thr Ser Ser Ala Glu Thr Ser Ala
            100                 105                 110

Gln Val Thr Ser Ser Val Gln Glu Thr Ser Ser Ser Ala Glu Glu Gln
            115                 120                 125

Val Thr Gln Ser Ser Ser Ser Ser Pro Ser Ser Ser Ser Ser Ser
130                 135                 140

Ser Ser Gly Ser Ser Ser Gly Ser Ser Ser Gly Ile Asp Gly Asp
145                 150                 155                 160

Leu Ser Trp Tyr Ser Gly Pro Gly Asn Lys Phe Gln Asp Gly Thr Ile
                165                 170                 175

Lys Cys Ser Glu Phe Pro Ser Gly Asn Gly Val Val Ala Leu Asp His
            180                 185                 190

Leu Gly Phe Gly Gly Trp Ser Gly Leu Tyr His Pro Ser Asp Thr Ser
            195                 200                 205

Thr Gly Gly Ile Cys Glu Pro Asp Thr Tyr Cys Ser Tyr Ala Cys Gln
            210                 215                 220

Ser Gly Met Ser Lys Thr Gln Trp Pro Ser Glu Gln Pro Asp Asn Gly
225                 230                 235                 240

Val Ser Val Gly Gly Leu Tyr Cys Asp Ser Asp Gly Tyr Leu Tyr Arg
                245                 250                 255

Ser Lys Thr Asp Thr Asp Tyr Leu Cys Glu Trp Gly Ile Asp Val Ala
            260                 265                 270

Tyr Val Val Ser Glu Ile Gly Lys Thr Ala Ala Ile Cys Arg Thr Asp
```

```
                275                 280                 285
Tyr Pro Gly Thr Glu Asn Met Val Ile Pro Thr Val Thr Pro Gly
    290                 295                 300

Gly Glu Leu Pro Leu Thr Thr Val Asp Gln Ser Ser Tyr Tyr Thr Trp
305                 310                 315                 320

Arg Gly Met Lys Thr Ser Ala Gln Tyr Tyr Val Asn Asp Ala Gly Val
                325                 330                 335

Asp Trp Thr Thr Gly Cys Thr Trp Gly Asp Tyr Gly Thr Asp Tyr Gly
                340                 345                 350

Asn Trp Ala Pro Leu Asn Phe Gly Ala Gly Tyr Asp Asn Gly Ile Ser
                355                 360                 365

Tyr Leu Ser Leu Ile Pro Asn Pro Asn Asn Lys Asp Thr Met Asn Tyr
        370                 375                 380

Asn Val Lys Ile Val Ala Tyr Asp Asp Ser Ser Val Val Ile Gly Glu
385                 390                 395                 400

Cys Lys Tyr Glu Asn Gly Ser Tyr Asn Gly Asn Gly Ser Asp Gly Cys
                405                 410                 415

Thr Val Ala Val Asn Ser Gly Lys Ala Lys Phe Val Leu Tyr
                420                 425                 430

<210> SEQ ID NO 23
<211> LENGTH: 313
<212> TYPE: PRT
<213> ORGANISM: Komagataella pastoris

<400> SEQUENCE: 23

Met Lys Phe Ser Thr Asn Leu Ile Leu Ala Ile Ala Ala Ala Ser Thr
1               5                   10                  15

Val Val Ser Ala Ala Pro Val Ala Pro Ala Glu Glu Ala Ala Asn His
                20                  25                  30

Leu His Lys Arg Ala Tyr Tyr Thr Asp Thr Thr Lys Thr His Thr Phe
            35                  40                  45

Thr Glu Val Val Thr Val Tyr Arg Thr Leu Lys Pro Gly Glu Ser Ile
    50                  55                  60

Pro Thr Gly Ser Pro Ser His Gly Gly Lys Gly Ser Lys Thr Gly Lys
65                  70                  75                  80

Gly Lys Gly Ser Thr Thr Asp Ala Gly Val Pro Gly Thr Thr Ser Val
                85                  90                  95

Ala Pro Thr Ala Asp Ser Thr Ser Ala Ser Gly Ser Ile Gly Leu Pro
            100                 105                 110

Thr Ser Ala Ser Ser Ala Thr Ser Ala Thr Ser Ser Ala Ser Thr Thr
        115                 120                 125

Thr Ser Gly Thr Ser Thr Ser Ser Thr Gly Thr Gly Thr Thr Thr Gly
    130                 135                 140

Ala Thr Thr Gly Thr Gly Thr Ser Ser Thr Gly Thr Thr Ser Ser Ser
145                 150                 155                 160

Thr Ser Ser Ser Ala Thr Ser Thr Pro Thr Gly Ser Leu Asp Ala Ile
                165                 170                 175

Ser Gln Ser Leu Leu Asp Thr His Asn Glu Lys Arg Ala Leu His Gly
            180                 185                 190

Val Ser Asp Leu Thr Trp Ser Thr Glu Leu Ala Asp Tyr Ala Gln Gly
        195                 200                 205

Tyr Ala Asp Ser Phe Thr Cys Gly Ser Ser Leu Val His Thr Gly Gly
    210                 215                 220
```

```
Pro Tyr Gly Glu Asn Leu Ala Ser Gly Tyr Ser Pro Ala Gly Ser Val
225                 230                 235                 240

Glu Ala Trp Tyr Asn Glu Ile Ser Asp Tyr Asp Phe Ser Asn Pro Gly
            245                 250                 255

Tyr Ser Ala Gly Thr Gly His Phe Thr Gln Val Val Trp Lys Ser Thr
        260                 265                 270

Thr Gln Leu Gly Cys Gly Tyr Lys Glu Cys Gly Thr Asn Arg Tyr Tyr
    275                 280                 285

Ile Ile Cys Glu Tyr Ala Pro Arg Gly Asn Ile Val Ser Ala Gly Tyr
290                 295                 300

Phe Glu Asp Asn Val Leu Pro Leu Val
305                 310
```

<210> SEQ ID NO 24
<211> LENGTH: 389
<212> TYPE: PRT
<213> ORGANISM: Saccharomyces cerevisiae

<400> SEQUENCE: 24

```
Met Arg Phe Ser Asn Phe Leu Thr Val Ser Ala Leu Leu Thr Gly Ala
1               5                   10                  15

Leu Gly Ala Pro Ala Val Arg His Lys His Glu Lys Arg Asp Val Val
            20                  25                  30

Thr Ala Thr Val His Ala Gln Val Thr Val Val Ser Gly Asn Ser
        35                  40                  45

Gly Glu Thr Ile Val Pro Val Asn Glu Asn Ala Val Val Ala Thr Thr
    50                  55                  60

Ser Ser Thr Ala Val Ala Ser Gln Ala Thr Thr Ser Thr Leu Glu Pro
65                  70                  75                  80

Thr Thr Ser Ala Asn Val Val Thr Ser Gln Gln Gln Thr Ser Thr Leu
                85                  90                  95

Gln Ser Ser Glu Ala Ala Ser Thr Val Gly Ser Ser Thr Ser Ser Ser
            100                 105                 110

Pro Ser Ser Ser Ser Ser Thr Ser Ser Ser Ala Ser Ser Ser Ala Ser
        115                 120                 125

Ser Ser Ile Ser Ala Ser Gly Ala Lys Gly Ile Thr Tyr Ser Pro Tyr
    130                 135                 140

Asn Asp Asp Gly Ser Cys Lys Ser Thr Ala Gln Val Ala Ser Asp Leu
145                 150                 155                 160

Glu Gln Leu Thr Gly Phe Asp Asn Ile Arg Leu Tyr Gly Val Asp Cys
                165                 170                 175

Ser Gln Val Glu Asn Val Leu Gln Ala Lys Thr Ser Ser Gln Lys Leu
            180                 185                 190

Phe Leu Gly Ile Tyr Tyr Val Asp Lys Ile Gln Asp Ala Val Asp Thr
        195                 200                 205

Ile Lys Ser Ala Val Glu Ser Tyr Gly Ser Trp Asp Asp Ile Thr Thr
    210                 215                 220

Val Ser Val Gly Asn Glu Leu Val Asn Gly Gly Ser Ala Thr Thr Thr
225                 230                 235                 240

Gln Val Gly Glu Tyr Val Ser Thr Ala Lys Ser Ala Leu Thr Ser Ala
                245                 250                 255

Gly Tyr Thr Gly Ser Val Val Ser Val Asp Thr Phe Ile Ala Val Ile
            260                 265                 270

Asn Asn Pro Asp Leu Cys Asn Tyr Ser Asp Tyr Met Ala Val Asn Ala
        275                 280                 285
```

```
His Ala Tyr Phe Asp Glu Asn Thr Ala Ala Gln Asp Ala Gly Pro Trp
        290                 295                 300

Val Leu Glu Gln Ile Glu Arg Val Tyr Thr Ala Cys Gly Gly Lys Lys
305                 310                 315                 320

Asp Val Val Ile Thr Glu Thr Gly Trp Pro Ser Lys Gly Asp Thr Tyr
                325                 330                 335

Gly Glu Ala Val Pro Ser Lys Ala Asn Gln Glu Ala Ala Ile Ser Ser
            340                 345                 350

Ile Lys Ser Ser Cys Gly Ser Ser Ala Tyr Leu Phe Thr Ala Phe Asn
        355                 360                 365

Asp Leu Trp Lys Asp Asp Gly Gln Tyr Gly Val Glu Lys Tyr Trp Gly
    370                 375                 380

Ile Leu Ser Ser Asp
385

<210> SEQ ID NO 25
<211> LENGTH: 386
<212> TYPE: PRT
<213> ORGANISM: Saccharomyces cerevisiae

<400> SEQUENCE: 25

Met Arg Leu Ser Asn Leu Ile Ala Ser Ala Ser Leu Leu Ser Ala Ala
1               5                   10                  15

Thr Leu Ala Ala Pro Ala Asn His Glu His Lys Asp Lys Arg Ala Val
            20                  25                  30

Val Thr Thr Thr Val Gln Lys Gln Thr Thr Ile Ile Val Asn Gly Ala
        35                  40                  45

Ala Ser Thr Pro Val Ala Ala Leu Glu Glu Asn Ala Val Val Asn Ser
    50                  55                  60

Ala Pro Ala Ala Ala Thr Ser Thr Thr Ser Ser Ala Ala Ser Val Ala
65                  70                  75                  80

Thr Ala Ala Ala Ser Ser Ser Glu Asn Asn Ser Gln Val Ser Ala Ala
                85                  90                  95

Ala Ser Pro Ala Ser Ser Ser Ala Ala Thr Ser Thr Gln Ser Ser Ser
            100                 105                 110

Ser Ser Gln Ala Ser Ser Ser Ser Ser Gly Glu Asp Val Ser Ser
        115                 120                 125

Phe Ala Ser Gly Val Arg Gly Ile Thr Tyr Thr Pro Tyr Glu Ser Ser
130                 135                 140

Gly Ala Cys Lys Ser Ala Ser Glu Val Ala Ser Asp Leu Ala Gln Leu
145                 150                 155                 160

Thr Asp Phe Pro Val Ile Arg Leu Tyr Gly Thr Asp Cys Asn Gln Val
                165                 170                 175

Glu Asn Val Phe Lys Ala Lys Ala Ser Asn Gln Lys Val Phe Leu Gly
            180                 185                 190

Ile Tyr Tyr Val Asp Gln Ile Gln Asp Gly Val Asn Thr Ile Lys Ser
        195                 200                 205

Ala Val Glu Ser Tyr Gly Ser Trp Asp Asp Val Thr Thr Val Ser Ile
    210                 215                 220

Gly Asn Glu Leu Val Asn Gly Asn Gln Ala Thr Pro Ser Gln Val Gly
225                 230                 235                 240

Gln Tyr Ile Asp Ser Gly Arg Ser Ala Leu Lys Ala Ala Gly Tyr Thr
                245                 250                 255

Gly Pro Val Val Ser Val Asp Thr Phe Ile Ala Val Ile Asn Asn Pro
```

```
                    260                 265                 270
Glu Leu Cys Asp Tyr Ser Asp Tyr Met Ala Val Asn Ala His Ala Tyr
                275                 280                 285

Phe Asp Lys Asn Thr Val Ala Gln Asp Ser Gly Lys Trp Leu Leu Glu
            290                 295                 300

Gln Ile Gln Arg Val Trp Thr Ala Cys Asp Gly Lys Lys Asn Val Val
305                 310                 315                 320

Ile Thr Glu Ser Gly Trp Pro Ser Lys Gly Glu Thr Tyr Gly Val Ala
                325                 330                 335

Val Pro Ser Lys Glu Asn Gln Lys Asp Ala Val Ser Ala Ile Thr Ser
            340                 345                 350

Ser Cys Gly Ala Asp Thr Phe Leu Phe Thr Ala Phe Asn Asp Tyr Trp
                355                 360                 365

Lys Ala Asp Gly Ala Tyr Gly Val Glu Lys Tyr Trp Gly Ile Leu Ser
            370                 375                 380

Asn Glu
385

<210> SEQ ID NO 26
<211> LENGTH: 420
<212> TYPE: PRT
<213> ORGANISM: Saccharomyces cerevisiae

<400> SEQUENCE: 26

Met Lys Leu Ser Ala Thr Thr Leu Thr Ala Ala Ser Leu Ile Gly Tyr
1               5                   10                  15

Ser Thr Ile Val Ser Ala Leu Pro Tyr Ala Ala Asp Ile Asp Thr Gly
                20                  25                  30

Cys Thr Thr Thr Ala His Gly Ser His Gln His Lys Arg Ala Val Ala
            35                  40                  45

Val Thr Tyr Val Tyr Glu Thr Val Thr Val Asp Lys Asn Gly Gln Thr
        50                  55                  60

Val Thr Pro Thr Ser Thr Glu Ala Ser Ser Thr Val Ala Ser Thr Thr
65                  70                  75                  80

Thr Leu Ile Ser Glu Ser Ser Val Thr Lys Ser Ser Lys Val Ala
                85                  90                  95

Ser Ser Ser Glu Ser Thr Glu Gln Ile Ala Thr Thr Ser Ser Ser Ala
            100                 105                 110

Gln Thr Thr Leu Thr Ser Ser Glu Thr Ser Thr Ser Glu Ser Ser Val
        115                 120                 125

Pro Ile Ser Thr Ser Gly Ser Ala Ser Thr Ser Ser Ala Ala Ser Ser
            130                 135                 140

Ala Thr Gly Ser Ile Tyr Gly Asp Leu Ala Asp Phe Ser Gly Pro Tyr
145                 150                 155                 160

Glu Lys Phe Glu Asp Gly Thr Ile Pro Cys Gly Gln Phe Pro Ser Gly
                165                 170                 175

Gln Gly Val Ile Pro Ile Ser Trp Leu Asp Glu Gly Trp Ser Gly
            180                 185                 190

Val Glu Asn Thr Asp Thr Ser Thr Gly Gly Ser Cys Lys Glu Gly Ser
        195                 200                 205

Tyr Cys Ser Tyr Ala Cys Gln Pro Gly Met Ser Lys Thr Gln Trp Pro
    210                 215                 220

Ser Asp Gln Pro Ser Asp Gly Arg Ser Ile Gly Gly Leu Leu Cys Lys
225                 230                 235                 240
```

-continued

Asp Gly Tyr Leu Tyr Arg Ser Asn Thr Asp Thr Asp Tyr Leu Cys Glu
                245                 250                 255

Trp Gly Val Asp Ala Ala Tyr Val Val Ser Glu Leu Ser Asn Asp Val
            260                 265                 270

Ala Ile Cys Arg Thr Asp Tyr Pro Gly Thr Glu Asn Met Val Ile Pro
        275                 280                 285

Thr Tyr Val Gln Ala Gly Asp Ser Leu Pro Leu Thr Val Val Asp Gln
    290                 295                 300

Asp Thr Tyr Tyr Thr Trp Gln Gly Leu Lys Thr Ser Ala Gln Tyr Tyr
305                 310                 315                 320

Val Asn Asn Ala Gly Ile Ser Val Glu Asp Ala Cys Val Trp Gly Ser
                325                 330                 335

Ser Ser Ser Gly Val Gly Asn Trp Ala Pro Leu Asn Phe Gly Ala Gly
            340                 345                 350

Ser Ser Asp Gly Val Ala Tyr Leu Ser Leu Ile Pro Asn Pro Asn Asn
        355                 360                 365

Gly Asn Ala Leu Asn Phe Asn Val Lys Ile Val Ala Ala Asp Asp Ser
    370                 375                 380

Ser Thr Val Asn Gly Glu Cys Ile Tyr Glu Asn Gly Ser Phe Ser Gly
385                 390                 395                 400

Gly Ser Asp Gly Cys Thr Val Ser Val Thr Ala Gly Lys Ala Lys Phe
                405                 410                 415

Val Leu Tyr Asn
            420

<210> SEQ ID NO 27
<211> LENGTH: 26
<212> TYPE: DNA
<213> ORGANISM: Artificial Sequence
<220> FEATURE:
<223> OTHER INFORMATION: Primer

<400> SEQUENCE: 27
cgcctcgaca tcatctgccc agatgc                                        26

<210> SEQ ID NO 28
<211> LENGTH: 26
<212> TYPE: DNA
<213> ORGANISM: Artificial Sequence
<220> FEATURE:
<223> OTHER INFORMATION: Primer

<400> SEQUENCE: 28
cgggcgacag tcacatcatg ccccrg                                        26

<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
ggccagaatg taaacaaatg cagataagg                                     29

<210> SEQ ID NO 30
<211> LENGTH: 17
<212> TYPE: DNA
<213> ORGANISM: Artificial Sequence
<220> FEATURE:
<223> OTHER INFORMATION: Primer

```
<400> SEQUENCE: 30
cgtcactgcc agcagtg                                                      17

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
gctgccttcc ctatatctga tatcac                                            26
```